(12) United States Patent
Stracher et al.

(10) Patent No.: US 7,968,516 B2
(45) Date of Patent: Jun. 28, 2011

(54) TREATMENT OF MULTIPLE SCLEROSIS AND OTHER AUTOIMMUNE DISEASES BY USE OF CALPIN INHIBITORS

(75) Inventors: Alfred Stracher, Roslyn, NY (US); Leo Kesner, West Orange, NJ (US)

(73) Assignee: ProTor Pharma Corporation, Roslyn, NY (US)

( * ) Notice: Subject to any disclaimer, the term of this patent is extended or adjusted under 35 U.S.C. 154(b) by 276 days.

(21) Appl. No.: 11/663,666

(22) PCT Filed: Sep. 29, 2005

(86) PCT No.: PCT/US2005/035712
§ 371 (c)(1),
(2), (4) Date: Apr. 30, 2008

(87) PCT Pub. No.: WO2006/037133
PCT Pub. Date: Apr. 6, 2006

(65) Prior Publication Data
US 2008/0200399 A1      Aug. 21, 2008

Related U.S. Application Data

(60) Provisional application No. 60/614,309, filed on Sep. 29, 2004.

(51) Int. Cl.
*A61K 38/06*      (2006.01)
*A61K 38/00*      (2006.01)
(52) U.S. Cl. .................... 514/17.9; 514/21.9
(58) Field of Classification Search .................. None
See application file for complete search history.

(56) References Cited

FOREIGN PATENT DOCUMENTS

| EP | 0279887 | * | 8/1988 |
| EP | 1454627 | * | 9/2004 |

OTHER PUBLICATIONS

Di Rosa G, Odrljin T, Nixon RA, Arancio O, "Calpain Inhibitors," Journal of Molecular Neuroscience, Oct. 2002, 19 (1-2): 135-141.*
Neurological Degeneration from http://www.northshore.org/clinicalservices/medicalgenetics/hereditaryconditions/default.aspx?id=4423, pp. 1-2. Accessed Jul. 6, 2009.*
Retinitis Pigmentosa from http://emedicine.medscape.com/article/1227488-overview, pp. 1-6. Accessed Jul. 6, 2009.*
Cataracts from http://www.allaboutvision.com/conditions/cataracts.htm, pp. 1-3. Accessed Jul. 6, 2009.*
What is Alzheimer's from http://alz.org/alzheimers_disease_what_is_alzheimers.asp, pp. 1-4. Accessed Jul. 6, 2009.*
Huntington's Disease from http://www.ninds.nih.gov/disorders/huntington/huntington.htm, pp. 1-2. Accessed Jul. 6, 2009.*
What is a stroke from http://www.stroke.org/site/PageServer?pagename=STROKE, pp. 1-2. Accessed Jul. 6, 2009.*
Spinal Cord injury from http://www.faqs.org/health/Sick-V4/Spinal-Cord-Injury.html, pp. 1-6. Accessed Jul. 6, 2009.*
Pepstatin structure from http://www.mpbio.com/product_info.php?products_id=195368, pp. 1-3. Accessed Jul. 6, 2009.*
Chymostatin structure from http://www.sigmaaldrich.com/etc/medialib/docs/Sigma/Product_Information_Sheet/c7268pis.Par.0001.File.tmp/c7268pis.pdf, pp. 1-2. Accessed Jul. 6, 2009.*
Alzheimer disease from Merck manual, pp. 1-17. Accessed Jul. 29, 2009.*
Mattson MP, "Pathways towards and away from Alzheimer's disease," Nature, 2004, 430: 631-639.*
Huntington's disease from Merck manual, pp. 1-2. Accessed Mar. 14, 2010.*
Parkinson's disease from Merck manual, pp. 1-10. Accessed Mar. 14, 2010.*
Multiple sclerosis from NIH, pp. 1-4. Accessed Mar. 14, 2010.*
Steinman L, Zamvil SS, "How to successfully apply animal studies in experimental allerfic encephalomyelitis to research on multiple sclerosis," Ann Neurol, 2006, 60: 12-21.*
Sriram S, Steiner I, "Experimental allerfic encephalomyelitis: a misleading model of multiple sclerosis," Ann Neurol, 2005, 58: 939-945.*
Han H-K, "Targeted prodrug design to optimize drug delivery," AAPS Pharmsci, 2000, 2(1): 1-11.*

* cited by examiner

*Primary Examiner* — Julie Ha
(74) *Attorney, Agent, or Firm* — Pearl Cohen Zedek Latzer, LLP

(57) ABSTRACT

Described herein are compounds and methods for treating or preventing a neurologic, otologic, or ophthalmologic disease in a subject. Also described herein are compounds that can be used as therapeutics.

10 Claims, 13 Drawing Sheets

Synthesis of CLA and CLA Acetal

Generic Synthesis of Linked Cysteic Acid/Leucyl-Argininal Calpain Inhibitor Compounds

Generic Synthesis of Linked Cysteic Acid/Aldehyde Calpain Inhibitor Compounds

A

B

C

A

B

C

A. CFA control calpain    B. EAE calpain    C. CLA-treated calpain

D. CFA control CD 11b    E. EAE CD 11b    F. CLA-treated CD 11b

G. CFA control CD 45    H. EAE CD 45    I. CLA-treated CD 45

A. Normal, LFB staining

B. EAE, LFB staining

C. CLA-treated, LFB staining

E. Normal, APP staining

E. EAE, APP staining

F. CLA-treated, APP staining

TREATMENT OF MULTIPLE SCLEROSIS AND OTHER AUTOIMMUNE DISEASES BY USE OF CALPIN INHIBITORS

CROSS REFERENCE TO RELATED APPLICATIONS

This application claims the priority of U.S. provisional application Ser. No. 60/614,309 filed on Sep. 29, 2004, which application is hereby incorporated herein by this reference in its entirety, for all of its teachings.

ACKNOWLEDGMENTS

Some of the inventions disclosed herein were made with government support under Grant Nos. 1R41NS039222-01 and 1R41DC006371-01A1 awarded by National Institutes of Health. The government may have rights in certain inventions disclosed herein.

BACKGROUND

Neurologic, and neurologically related otologic, and ophthalmologic diseases can be very debilitating and/or fatal to the patient, whether induced by various forms of disease or stroke, or various forms of trauma, because the repair and/or regeneration of damaged neurons is often difficult or impossible. Various naturally occurring protease enzymes are believed to be part of the basic machinery of cellular catabolism and part of the mechanism of neuronal cell death pathways (see Nakanishi et al., reference 28).

Although much research has been focused on the prevention and treatment of such neurologic, and neurologically related otologic, and ophthalmologic diseases or injuries, whether caused by trauma, stroke, ischemia, or various immunological and/or degenerative disease processes, the successful development of treatments for such neurologically related diseases have been limited, and there remains a long-felt and unmet need in the art for improved treatments of such neurologically related diseases.

Calcium-activated neutral proteases ("Calpains") refers to a family of structurally related heterodimeric neutral and non-lysosomal $Ca^{2+}$ activated cysteine proteases that are found in all tissue and cell types. Calpains are believed to be involved in important signaling pathways, modulation of enzyme activity, processing of hormones, protein turnover, and cytoskeletal rearrangements. See "The Calpain System" by Goll et al., (59), and Ray et al., (67). Calpains are typically cytosolic proteolytic enzymes that become activated against a number of cytosolic and membrane proteins, cytokines, transcriptional factors, kinases, phosphatases, and lens proteins, when increased levels of intracellular free $Ca^{2+}$ions are present (micromolar levels for "μ-calpains" and millimolar concentrations for "m-calpains"). Calpains are also believed to be involved in many cellular death processes initiated by various traumas, ischemia, and immunological and inflammation-induced diseases, as well as a variety of central nervous system diseases wherein various cellular and/or membrane defects and/or injuries affect the cellular homeostasis of calcium ions, leading to increased concentrations of intracellular calcium ions and the activation of the calpains. Calpains are believed to be involved in a variety of degenerative diseases of the central nervous system, including stroke and related ischemic diseases, spinal cord injuries, traumatic brain injuries, retinal degeneration, cataracts, antibiotic-induced ototoxicity, Alzheimer's disease, amyotrophic lateral sclerosis (ALS, Lou Gehrig's disease), Huntington's disease, Parkinson's disease, spinocerebellar atrophies, multiple sclerosis, inflammatory demyelinating polyneuropathy, and other polyneuropathies.

One degenerative neurologic disease that is particularly devastating is multiple sclerosis ("MS"). Multiple sclerosis is an autoimmune, neurodegenerative disease that affects about 350,000 people in the United States and is a major cause of nervous system disability or death in young adults (see references 11, 14, and 23). A common clinical condition in humans afflicted with MS is inflammation of the central nervous system ("CNS") white matter, and the degenerative formation of neural lesions resulting from extensive degradation of the myelin sheaths surrounding the axons of the neurons, and eventual degradation of the axons themselves. The demyelination that occurs in MS is believed to be initiated by the attack of protease enzymes on three major neurological proteins: myelin basic protein (MBP), proteo-lipid protein (PLP) and myelin oligodendrocyte glycoprotein (MOG). Mechanistically, MS is an inflammatory demyelinating disease that is at least partially caused by an autoimmune response to myelin degradation products (6, 7, 13, 24, 26, 32, 48, 55, 56). Recent studies have emphasized the role of axonal injury in addition to the well known demyelation and inflammatory mechanisms.

Peptides derived from the MBP, PLP, and MOG neurological proteins can have the properties of encephalitogenic epitopes, and can be used to induce experimental autoimmune encephalomyelitis (EAE) in mice, which is well known as a valuable animal model for MS (1, 9, 12, 18, 24, 25, 29, 43, 46, 47, 52, 45, 55). A combination of adoptive transfer of MBP-specific T-cells (26,32, 57) and/or active immunization of mice with encephalitogenic peptide derived from MOG, often in the presence of immunogenic adjuvants (17, 24, 27) initiate an immune response and result in the demyelination of neurons in the mice, to provide the EAE animal model of the similar demyelination observed during MS. Activated T-cells are believed to constitute only a small fraction of the total inflammatory cells in the central nervous system of mice with acute EAE, or humans with MS. The T-cells recruit a large population of macrophage cells. In addition, the microglia, which serve as macrophages in the brain and spinal cord of the central nervous system, are also activated. The macrophages and microglia present in both EAE and MS induce damage to the myelin of neurons in large part via their proteolytic activity.

Calpain is activated in the CNS tissue of animals with EAE (8, 44, 45), in patients with MS (33, 34), and during myelinolysis (28, 35-37, 40, 41, 43). Calpain is significantly elevated in the white matter of MS patients and is increasingly expressed in activated microglia and macrophages in MS patients. Although other proteases may also be involved in myelin degradation, recent studies suggest that calpains play a major role in this process in the EAE model (22, 30, 26-39, 41, 43, 46, 47). Inhibition of calpain activity should limit the ultimate pathology in both EAE and MS and other diseases involving proteolytic demyelination and neurodegeration.

Some studies have demonstrated calpain inhibition with the tripeptide protease inhibitor leupeptin in peripheral nerve (2-6), and leupeptin's effect in suppressing EAE in rats (29). It has also been shown that leupeptin protects cochlear and vestibular hair from gentamycin oxotoxicity (6, 10). Leupeptin's structure is shown below:

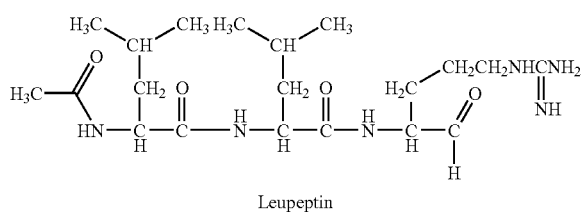

Leupeptin

However, among the limitations of leupeptin in these clinical applications is its poor cellular permeability, including a poor ability to cross the blood brain barrier (BBB) to reach desired sites of action within the central nervous system (CNS). Leupeptin can be transported across the BBB and into the CNS by liposome encapsulation (29), but this method is technically difficult and impractical for routine use. Moreover, leupeptin and other known small molecule protease inhibitors are not very selective, since they typically inhibit the proteases in many non-diseased tissues in the body, including serine proteases. Therefore, a method of treatment of MS and other nervous and central nervous system degenerative diseases wherein therapeutic agents (such as calpain inhibitors) are efficiently transferred across the BBB and targeted to their site of action within the central nervous system is highly desirable.

Taurine (2-aminethanesulfonic acid, structure shown below) is the most abundant free amino acid in many tissues including leukocytes and brain, where it is present in millimolar concentrations (15, 16, 31, 34, 42). The brain synthesizes only limited amounts of taurine and thus significant amounts must be transported into those parts of the brain and central nervous system that require it (19). Taurine is believed to be transported into cells via a $Na^+$-dependent transport system (16), and two distinct $Na^+$-dependent high affinity taurine transporters have been cloned.

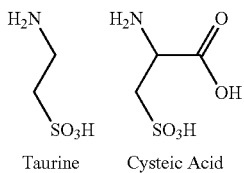

Taurine    Cysteic Acid

Cysteic acid (α-amino-β-sulfo-propionic acid) shares structural similarities with taurine. It is a competitive inhibitor of taurine transport and thus utilizes the same transport mechanisms (20, 21). Cysteic acid has a carboxyl group in addition to the sulfonic acid and amino groups of taurine, which provides another functional group to which other protease inhibitor residues can be attached. U.S. Pat. Nos. 4,866,040, and 5,008,288 disclosed the synthesis of a compound in which a leucyl-argininal residue was attached to cysteic acid, and disclosed that such compounds could "be useful for specific delivery to a variety of tissues such as cardiac and skeletal muscle, nervous tissue, adrenal medulla, platelets, etc." Those patents did not, however, further elaborate on the specific neurological disorders to be treated, provide any details how such treatments should be carried out, or demonstrate that any such speculated treatments actually work successfully. These patents also did not elaborate on the potential advantages of using a calpain inhibitor conjugated to cysteic acid for the purpose of treating neurological diseases triggered by an autoimmune response, such as multiple sclerosis. In such autoimmune neurodegenerative diseases, the enhanced uptake of cysteic acid conjugates by leukocytes may provide an unexpected benefit, by inhibiting active calpain that is released into diseased tissue as part of the undesired immune response, in addition to inhibiting calpain activity within neurons.

The development of improved small molecule calpain inhibitors has been the subject of a good deal of research (see Ray et al., 67), but "there has been no report yet showing the effectiveness of these inhibitors for inhibition of calpain in vivo," and "It should be emphasized that there are difficulties in developing small molecule inhibitors with the appropriate drug properties. Although calpain is an important drug discovery target, it has been proven to be a difficult one that may or may not be tractable." Thus, many have tried and failed to successfully develop calpain inhibitors, and there remains in the art a long felt and as yet unsatisfied need for the development of protease inhibitors that can be targeted to specific tissues to treat or prevent specific diseases, such as. stroke and related ischemic diseases, spinal cord injuries, traumatic brain injuries, retinal degeneration, cataracts, acoustic trauma due to loud noises, antibiotic-induced ototoxicity, multiple sclerosis, Alzheimer's disease, amyotrophic lateral sclerosis (ALS, Lou Gehrig's disease), Huntington's disease, Parkinson's disease, spinocerebellar atrophies and inflammatory demyelinating polyneuropathy.

To overcome these problems in the art, described herein below are compounds that facilitate the selective transport and/or concentration of protease inhibitors that can be bound thereto, such as, for example, calpain inhibitors, within nervous tissue involved in specific neurologically-related diseases.

SUMMARY

Described herein are compounds that comprise a taurine and/or cysteic acid residue and a residue of a protease or calpain inhibitor, which may be directly bonded to each other or indirectly bonded to each other, and pharmaceutically acceptable salts of such compounds. Many of the compounds of the invention comprise leucyl argininal residues in the form of the aldehyde which is believed to be effective to inhibit calpains, or be present in the form of acetal prodrug residues that can be converted, before, during, or after administration, to the aldehyde form of the compounds. One or more of the compounds of the invention or their pharmaceutically acceptable salts may be used to manufacture medicaments, kits, and/or pharmaceutical compositions for treating a variety of traumatic, ischemic, immunological, and neurodegenerative diseases related to or resulting from the activity of protease and/or calpains, and/or inhibiting the proteolytic activity of the protease inhibitors and/or calpains. In related aspects, the compounds, pharmaceutically acceptable salts, or the kits, pharmaceutical compositions or medicaments thereof can be used to provide methods for treating or preventing such neurologic, otologic, and/or ophthalmologic diseases in a subject, including a human subject. Also described herein are compounds that can be used as therapeutics. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Definitions

Figure 1A:
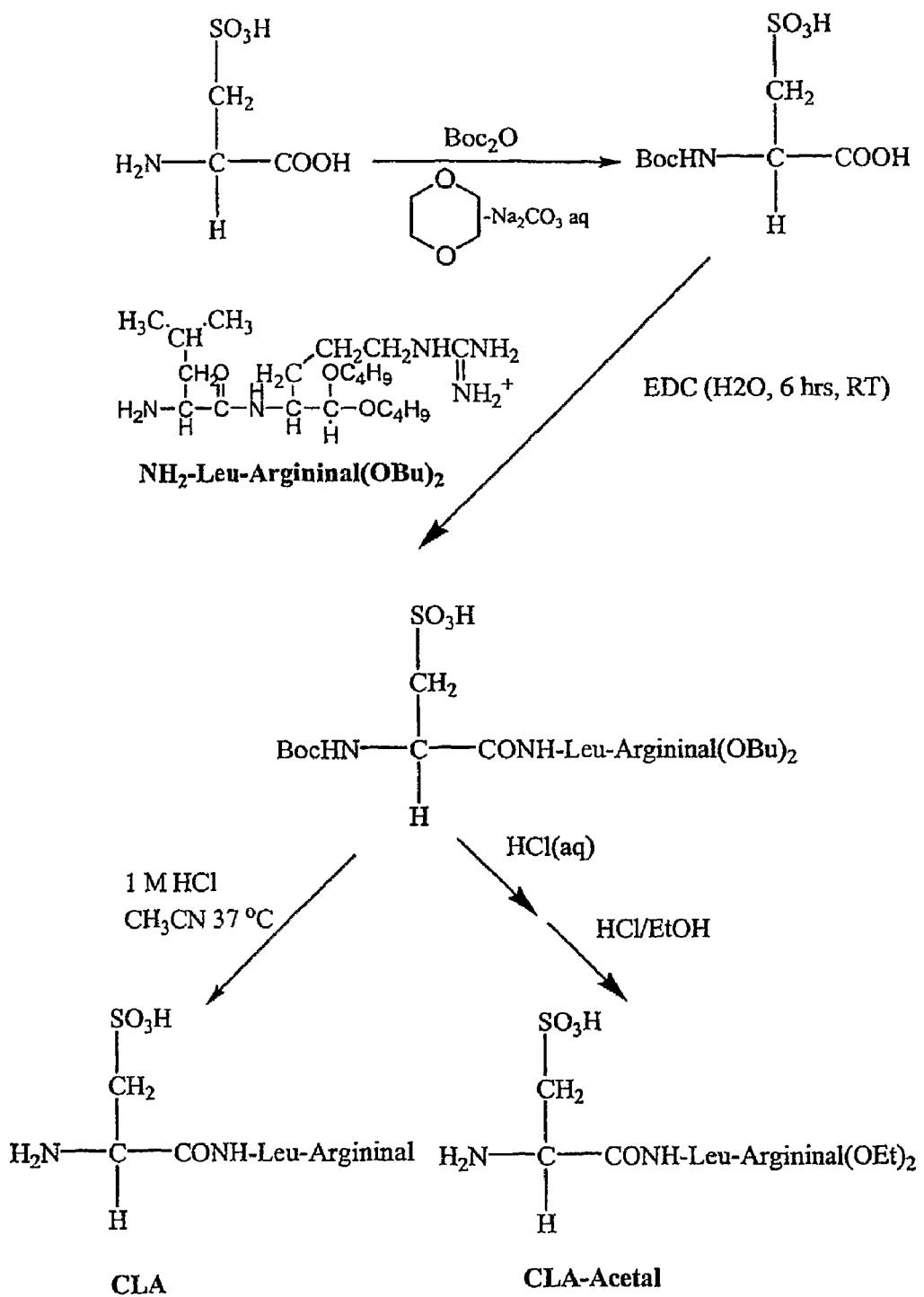
FIG. 1a shows the synthesis of cysteyl-leucyl-argininal ("CLA") and its diethylacetal prodrug form ("CLA-Acetal").

Before the present compounds, compositions, articles, and/or methods are disclosed and described, it is to be understood that the aspects described below are not limited to specific compounds, pharmaceutical compositions or kits, methods of treating diseases, synthetic methods, or as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

Variables such as $R^1$-$R^3$, m, L, W, X, Y, and Z used throughout the application are the same variables as previously defined unless stated to the contrary.

The term "residue" as used herein refers to the moiety that is the resulting product of the chemical species in a particular reaction scheme or subsequent formulation or chemical product, regardless of whether the moiety is actually obtained from the chemical species. For example, a linker L that contains at least one —OH group can be represented by the formula L-OH, where L is the remainder (i.e., residue) of the linker.

The term "organic residue" defines a carbon containing residue, i.e. a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic resides can preferably comprise 1 to 18 carbon atoms, 1 to 15 carbon atoms, 1 to 12 carbon atoms, 1 to 8 carbon atoms, or 1 to 4 carbon atoms.

A very close synonym of the term "residue" is the term "radical," which as used in the specification and concluding claims, refers to a fragment, group, or substructure of a molecule described herein, regardless of how the molecule is prepared. In some embodiments the radical (for example an alkyl) can be further modified (i.e., substituted alkyl) by having bonded thereto one or more "substituent radicals."

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "substituted alkyl" denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When more than one substituent group is present then they can be the same or different. The organic substituent groups can comprise from 1 to 12 carbon atoms, or from 1 to 6 carbon atoms, or from 1 to 4 carbon atoms.

The term "alkoxy" as used herein denotes an alkyl residue, defined above, attached directly to an oxygen to form an ether residue. Examples include methoxy, ethoxy, n-propoxy, iso-propoxy, n-butoxy, t-butoxy, iso-butoxy and the like.

The term "polyalkylene group" as used herein is a group having two or more $CH_2$ groups linked to one another. The polyalkylene group can be represented by the formula —$(CH_2)_o$—, where O is an integer of from 2 to 25.

The term "polyether group" as used herein is a group having the formula —$[(CHR)_oO]_p$— where R is hydrogen or a lower alkyl group, o is an integer of from 1 to 20, and p is an integer of from 1 to 100. Examples of polyether groups include polyethylene oxide, polypropylene oxide, and polybutylene oxide.

The term "polythioether group" as used herein is a group having the formula —$[(CHR)_oS]_p$—, where R is hydrogen or a lower alkyl group, o is an integer of from 1 to 20, and p is an integer of from 1 to 100.

The term "polyimino group" as used herein is a group having the formula —$[(CHR)_oNR]_p$—, where each R is, independently, hydrogen or a lower alkyl group, o is an integer of from 1 to 20, and p is an integer of from 1 to 100.

The term "polyester group" as used herein is a group that is produced by the reaction between a compound having at least two carboxylic acid groups with a compound having at least two hydroxyl groups.

The term "polyamide group" as used herein is a group that is produced by the reaction between a compound having at least two carboxylic acid groups with a compound having at least two unsubstituted or monosubstituted amino groups.

The term "aryl" denotes a ring radical containing 6 to 18 carbons, or preferably 6 to 12 carbons, having at least one six-membered aromatic "benzene" residue therein. Examples of such aryl radicals include phenyl and naphthyl. The term "substituted aryl" denotes an aryl ring radical as defined above that is substituted with one or more, or preferably 1, 2, or 3 organic or inorganic substituent groups, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups can comprise from 1 to 12 carbon atoms, or from 1 to 6 carbon atoms, or from 1 to 4 carbon atoms.

The term "heteroaryl" denotes an aryl ring radical as defined above, wherein at least one of the carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to hereinabove for aryl groups, bound to the carbon atoms of the heteroaromatic rings. The organic substituent groups can comprise from 1 to 12 carbon atoms, or from 1 to 6 carbon atoms, or from 1 to 4 carbon atoms.

The term "halo" or "halogen" refers to a fluoro, chloro, bromo or iodo group.

The term "protecting group" as used herein (and sometimes designated in the figures as (PG) is a group that can be chemically bound to an atom, and subsequently removed (either chemically, in vitro, or in vivo) from the atom by predictable methods. Examples of many of the possible protective groups can be found in *Protective Groups in Organic Synthesis* by T. W. Green, John Wiley and Sons, 1981, which is incorporated herein by reference in its entirety.

By "subject" is meant an individual. Preferably, the subject is a mammal such as a rodent, rat, or primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

"Treatment" or "treating" means to administer a composition to a subject or a system with an undesired condition. The effect of the administration of the composition to the subject can have the effect of, but is not limited to, reducing or preventing the symptoms of the condition, a reduction in the severity of the condition, or the complete ablation of the condition.

By "prevent" or "preventing" means the administration of a composition to a subject or a system at risk for an undesirable condition. The condition can include a disease or a predisposition to a disease. Prevention can range from a reduction in the severity of the condition to the complete ablation of the condition.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

By the term "effective amount" of a compound as provided herein is meant a sufficient amount of the compound or composition to provide the desired regulation of a desired function or outcome, such as protein activation or inhibition, or a disease condition or one of the physical or clinical manifestations thereof. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The term "neurologic disease" is any disease that adversely affects neural tissue. For example, an injury to the spinal cord or brain (i.e., direct injury to nervous tissue) can result in damage to neural tissue and, thus, produce a neurologic disease. The neurologic disease can be the result of one or more events including, but not limited to, injury to the central nervous system, degeneration of neural and non-neural tissue (e.g., age related or genetic predisposition to the neurologic disorder), and dystrophies associated with neural tissue.

Herein, "inhibition" means to reduce activity as compared to a control. It is understood that inhibition can mean a slight reduction in activity to the complete ablation of all activity. An "inhibitor" can be anything that reduces the targeted activity.

The term "prodrug" is defined herein as an inactive form of a parent drug that has been created to overcome one or more barriers to its effective use or absorption by subjects. For example, a prodrug can be a compound that has a protecting group that is cleaved upon administration to a subject to produce the active form of the drug.

Also, one or more compounds disclosed herein can include zwitterionic salts formed by reaction of a nitrogen contained internally within the compound, such as an amine, aniline, pyridyl, arginine, and like residues with an acidic hydrogen within the compound, such as the sulfonic acid groups. Alternatively, a basic nitrogen contained internally within the compound, such as the arginine or amine groups or residues can be reacted with a pharmaceutically acceptable external acid, such as HCl, sulfuric acid, a carboxylic acid or the like.

The term "otologic disease" is any disease that adversely affects hearing of a subject or tissue associated with the ear. Examples of otologic diseases include, but are not limited to traumatic hearing loss or antibiotic induced ototoxicity.

The term "ophthalmologic disease" is any disease that adversely affects the sight of a subject or tissue associated with the eye. Examples of ophthalmologic diseases include, but are not limited to, retinal degeneration, retinal injury, macular degeneration (wet and dry forms, dystrophies of the macula), retinitis pigmentosa, glaucoma, or cataracts.

Disclosed are compounds that can be used to prepare medicaments, pharmaceutical compositions, and kits thereof that can be used to treat a wide variety of the disclosed medical conditions and diseases. It is to be understood that when combinations, subsets, interactions, groups, etc. of these materials, uses, and methods are disclosed herein, while specific reference of each various individual and collective combinations and permutation of these compounds may not be explicitly disclosed, each is specifically contemplated and described herein. For example, if a number of different linkers, carrier molecules, and protease inhibitors are disclosed and discussed, each and every combination and permutation of the carrier molecules, linkers, and the protease inhibitor are contemplated hereby unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, while many such combinations are specifically disclosed in the specification and claims, if there are a variety of additional components listed, or steps that can be performed it is understood that each of these additional components and steps can be performed with any specific embodiment or combination of embodiments of the disclosed methods, and that each such combination is specifically contemplated and should be considered as described and disclosed.

I. Compounds of the Invention

Described herein are compounds and their pharmaceutically acceptable salts, which can be useful for the treatment of a variety of neurologic diseases induced by various causes, and neurologically-related otologic, and/or ophthalmologic diseases. The compounds of the invention vary in some aspects of their structures, but are also related in significant structural and functional aspects, because they comprise a cysteic acid residue and a residue of a protease or calpain inhibitor, which may be directly bonded to each other, or can be indirectly bonded via a variety of linker groups. The cysteic acid residues of the compounds of the invention can facilitate their targeting and/or active transport of the protease inhibitors across the blood/brain barrier and/or cellular membranes, and/or their selective concentration in the central and peripheral nervous tissues, and/or their selective concentration in leukocytes, whereby their desirable biological effects are maximized, and so that side effects in other tissues are minimized.

In one of many related aspects of the compounds of the invention, the compounds can have the formula I shown below:

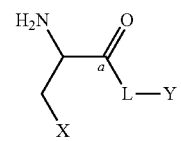

wherein L is a residue of an optional linker;
X is SO$_3$H or SO$_2$H; and
Y comprises a residue of a protease inhibitor;
or the pharmaceutically-acceptable salt thereof or the prodrug thereof,
wherein when L is not present and Y is bonded to carbon a.

In other related embodiments, the compounds of the invention have a linker group and have the formula II shown below:

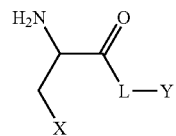

wherein L is a residue of a linker;
X is SO$_3$H or SO$_2$H; and
Y comprises a residue of a protease inhibitor;
or the pharmaceutically-acceptable salt thereof or the prodrug thereof.

In aspects of the compounds of formula II, the compounds have the formula (IIa) shown below:

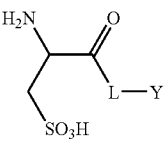

wherein L is a residue of a linker that is not —NH—; and
Y comprises a residue of a calpain inhibitor or a prodrug thereof;
or a pharmaceutically-acceptable salt thereof.

In yet another related aspect, the compounds of the invention can have the formula III shown below:

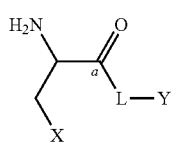

wherein L is a residue of an optional linker;
X is SO₃H or SO₂H; and
Y comprises a residue of a prodrug of a protease inhibitor; or the pharmaceutically-acceptable salt thereof,
wherein when L is not present and Y is bonded to a carbon a.

In many embodiments of such compounds of formulas (I), (II), and (III) recited above, X is often SO₃H or the SO₃⁻ anion derived therefrom. In some embodiments of the invention, the amine group (—NH₂) can react internally with the acidic hydrogen of the SO₃H or SO₂H groups, or reacted with external acids to form a cationic —NH₃⁺ ammonium group, so as to form an ammonium salt of the compound. In some embodiments of the compounds of formulas (I), (II), and (III) recited above, the —NH₂ amine group can be modified by alkylation, alkoxylation, or similar reactions with one, two, or three organic groups (especially alkyl groups or hydroxyalkyl groups) to generate N-substituted amines or ammonium salts.

The Protease Inhibitors

The term "protease inhibitor" is defined herein as any molecule or residue thereof that interacts with a protease enzyme and reversibly or irreversibly inhibits its proteolytic activity. The term "protease inhibitor" also includes prodrug or metabolic precursor molecules that can be converted to a protease inhibitor upon administration to a subject. In many aspects of the invention, the protease inhibitor is a calpain inhibitor. In one aspect, the protease inhibitor is a peptide aldehyde, a peptide boronate, or a vinyl sulfone. In another aspect, the protease inhibitor is a peptide having at least one aldehyde group or oxirane group.

Examples of protease inhibitors include, but are not limited to, pepstatin, bestatin, Bowman-Birk inhibitor, chymostatin, bacitracin, lactacystin, clasto-lactacystin-β-lactone, ritonavir, saquinavir, indinavir, nelfinavir, amprenavir, or the like. The protease inhibitors disclosed in Lee D. H. and Goldberg A. L. "Proteasome inhibitors: valuable new tools for cell biologist," Cell Biology, 8, 397-399, 1998; Goll D E, Thompson V F, Li H, Wei W, Cong J. "The calpain system," Physiol Rev. July 2003;83(3):731-801; Hernandez A A, Roush W R "Recent advances in the synthesis, design and selection of cysteine protease inhibitors," Curr Opin Chem Biol. August 2002;6(4):459-65; Perrin B J, Huttenlocher A. "Calpain," Int J Biochem Cell Biol. July 2002;34(7):722-5; Laval S H, Bushby K M "Limb-girdle muscular dystrophies—from genetics to molecular pathology," Neuropathol Appl Neurobiol. April 2004;30(2):91-105; Wagner K R "Genetic diseases of muscle" Neurol Clin. August 2002;20(3):645-78; Vanderklish P W, Bahr B A "The pathogenic activation of calpain: a marker and mediator of cellular toxicity and disease states" Int J Exp Pathol. October 2000;81(5):323-39; Hasselgren P O, Fischer J E "Muscle cachexia: current concepts of intracellular mechanisms and molecular regulation," Ann Surg. January 2001;233(1):9-17; Wang K K, Yuen P W "Calpain inhibition: an overview of its therapeutic potential," Trends Pharmacol Sci. November 1994;15(11):412-9; and Ray S K and Banik N L "Calpain and its involvement in the Pathophysiology of CNS injuries and diseases; Therapeutic potential of calpain inhibitors for prevention of neurodegeneration," Current Drug Targets-CNS and Neurological Disorders, 2, 173-189, 2003 (references 59-68), which are incorporated by reference in their entireties, can be used herein.

In many embodiments of the compounds of formulas I, II, and III, the protease inhibitor is a calpain inhibitor. Calpain inhibitors of the present invention are known and have been described in numerous scientific publications and patent literature. For example, U.S. Pat. No. 5,081,204 (Higuchi), U.S. Pat. No. 5,486,623 (Zimmerman), U.S. Pat. No. 5,498,616 (Mallamo), U.S. Pat. No. 5,506,243 (Ando), and U.S. Pat. No. 5,514,694 (Powers), and DePetrillo (see reference 80), describe a variety of different chemical entities for the inhibition of calpain including: N-substituted peptidyl compounds, peptidyl ketone heterocyclic ethers, heterocyclic-N-heteroatom methyl ketones, sulfonamide pyrolidines, and peptidyl ketoamides, respectively. Additional examples of calpain inhibitors in the patent literature include WIPO Publication Nos. WO 92/11850 (Cortex Pharmaceutical), WO 94/00095 (Cortex) and WO 95/00535 (Alkermes Inc.) which disclose peptide keto compounds, peptide aldehydes and alpha-ketoamides, respectively. Other examples of calpain inhibitors have been published in European Patent Application Publications. Still other calpain inhibitors in the scientific literature include alpha-mercaptoacrylic acids, disclosed in Proc. Natl. Acad. Sci. USA, volume 93, pages 6687-6692 (1996). Examples of calpain inhibitors include, but are not limited to, leucyl-argininal, benzamidine derivatives, leupeptin, PhCH₂OCO-leucine-norvaline-CONH—CH₂-2-pyridyl, Ph₂CHCO-leucine-alpha-aminobutyric acid-CONH—CH₂-2-pyridyl, Ph₂CHCO-leucine-alpha-aminobutyric acid-CONH—(CH₂)₃-4-morpholinyl, PhCH₂OCO-leucine-alpha-aminobutyric acid-CONH—CH₂-2-pyridyl, and PhCH₂OCO-leucine-alpha-aminobutyric acid-CONH—CH₂—CH(OH)Ph.

The protease and/or calpain inhibitor residues of many of the compounds of the invention comprise leucyl argininal dipeptide residues, wherein the argininal residue comprises an aldehyde residue. In many embodiments of the compounds of the invention, Y comprises a dipeptidyl leucyl-argininal residue whose structures are illustrated below,

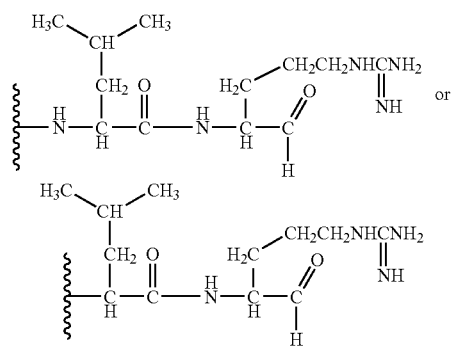

Moreover, those of ordinary skill in the art will appreciate that such argininal residues comprise a strongly basic terminal guanidine group that will often be, even at neutral pH's protonated to form a cationic residue as illustrated below:

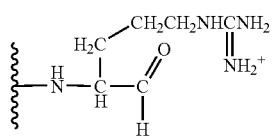

While not wishing to be bound by theory, the aldehyde group of the argininal residue is believed to be necessary to effectively inhibit the active site of calpains. Nevertheless, because of their high chemical reactivity, the presence of the aldehyde group can lead to stability problems in the resulting compound related to epimerization and/or racemization of the adjacent optically active carbon and concomitant loss of optical activity, condensation and/or cyclization side reactions, both in solutions or during manufacture, formulation, shipping, sale, and/or patient storage.

When a protease inhibitor comprises an aldehyde group, the aldehyde group can be converted to a group that can readily be converted back to the free aldehyde. For example, the aldehyde group can be converted to an acetal or hemiacetal using techniques known in the art, which can be cleaved under acidic conditions to produce the active form of the compound (i.e., reproduce the aldehyde group). In another aspect, the aldehyde can be converted to the corresponding bisulfite compound. The techniques disclosed in U.S. Pat. No. 5,436,229 for converting argininal aldehydes to bisulfite compounds, which is incorporated by reference in its entirety, can be used herein.

Therefore in some embodiments of the compounds of the invention, the disadvantageous chemical properties of aldehyde groups can be mitigated or overcome by making and formulating the compounds wherein aldehyde active residue in the form of an acetal prodrug residue, an example of which is shown below.

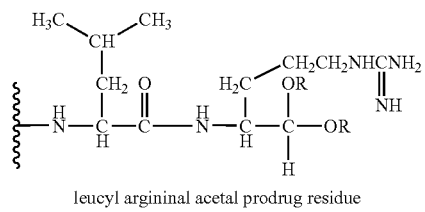

leucyl argininal acetal prodrug residue

The "R" groups bonded to the two acetal oxygen atoms that are shown in the drawing above can be derived from a variety of alcohol precursors, including methanol, ethanol, propanols etc. In various embodiments, the acetal R groups can be the same or different, and are branched- or straight-chain alkyl group having from 1 to 20 carbon atoms, 1 to 12 carbon atoms, 1 to 6 carbon atoms, or 1 to 3 carbon atoms. In some embodiments, the R groups of the acetal group can be independently selected from methyl, ethyl, propyl, isopropyl, butyl, isobutyl, pentyl, isopentyl, or hexyl. In some embodiments, the acetal group is part of a ring, for example when the alcohol used to form the acetal is a diol such as ethylene or propylene glycol. In many preferred embodiments, each acetal R group is an ethyl group.

It has been discovered that such acetal prodrug residues can be readily manufactured and stored without deleterious chemical reactions or decomposition, then converted by hydrolysis, before, during, or after administration to a subject, or by means of a kit, to the biologically active aldehyde form of the compounds. The acetal prodrug forms of the compounds can be converted to the biologically active aldehyde form of the compounds either in-vitro before administration, or very surprisingly, be converted in-vivo during and/or after administration to the free aldehyde form of the drug. Such in-vivo conversion of the acetal prodrug forms of the compounds of the invention to the biologically active form of the compound can be demonstrated by administration of the acetal prodrug form of the compound intravenously to suitable experimental mammals, such as C57BL/6J mice at a concentration of about 1 mg/kg, and after approximately 8 hours, the concentration of the aldehyde form of the compound in the retina is at least 15% of the concentration of acetal prodrug form of the compound, as measured by HPLC/Mass Spec analysis of filtered aqueous solutions of tissue homogenates.

Moreover, it appears that the acetal prodrugs can be used to make these often zwitterionic compounds more lipophilic, so as to aid the absorption and/or delivery of the compounds to the desired tissues.

The Cysteic Acid Carrier

The portion of the molecule in formulae I-III that is not the linker "L" and the protease inhibitor "Y" is a residue that corresponds to a derivative of cysteic acid, including organic ester, amide, or thioester derivatives of the carboxylic acid group of cysteic acid, which may be termed the "carrier molecule". Such derivatives of cysteic acid and their salts have the structures shown below:

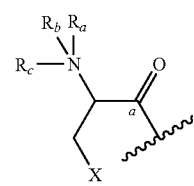

wherein X is $SO_3H$, $SO_3^-$, $SO_2H$, or $SO_2^-$ and $R_a$, $R_b$, and $R_c$ can be hydrogen or a $C_1$-$C_4$ organic substituent such as alkyl, and if $R_a$, $R_b$, and $R_c$ are all present the amine nitrogen atom forms a positively charged ammonium group.

Without wishing to be bound by theory, the cysteic acid carrier is believed to facilitate the active transport and/or absorption of the entire compound, including the protease inhibitor, into neural cells or tissues that normally have active transport mechanisms for taurine. This can lead to a substantial and unexpected clinical benefit, in that the compounds of the invention can thereby be selectively "targeted" to such tissues, such as the neurons of the central and peripheral nervous systems, and leukocytes and other cells of the immune system. A consequence of such "tissue targeting" is that compounds of the invention can be selectively concentrated in those tissues as compared to other tissues in the body wherein the inhibition of protease activity may be undesirable and/or cause undesirable side effects.

In order to identify compounds that exhibit this desirable "tissue targeting" property to greater and lesser degrees, the compound should be administered intravenously to suitable test mammals, such as the C57BL/6J mice which are suitable for EAE testing as described in the examples, at a concentration of about 1 mg/kg, and after approximately 8 hours (a time which can be suitably varied if the serum half life of the compound is much shorter or much longer than 8 hours), the concentration of the drug in tissues of interest that are known to accumulate taurine (such as rat retina) as detected by HPLC/Mass Spec analysis of filtered aqueous solutions of tissue homogenates should be compared with similar analysis tissues that are not believed to accumulate taurine (such as rat liver).

Candidate compounds that accumulate in rat retina by a concentration factor of at least two, or five, or 10 as compared to the reference tissue can be considered to be "targeted" compounds.

The cysteic acid carrier residue and the protease inhibitor residue can be directly or indirectly bonded to one another. When the carrier molecule and protease inhibitor are directly bonded to one another, a new covalent bond is formed between the carrier molecule and the protease inhibitor. In such embodiments, Y is directly bonded to the "a" carbon, and the compounds have the structure shown below:

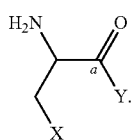

For example, the COOH group of cysteic acid can react with an amino group present on the protease inhibitor to form a new amide linkage, or react with an alcohol or thiol group on the protease inhibitor to form the corresponding carboxylic acid esters or thioesters. In one such embodiment wherein the cysteic acid and protease inhibitor residues are directly bonded, a compound that is particularly useful in the pharmaceutical applications described herein has the formula V:

V

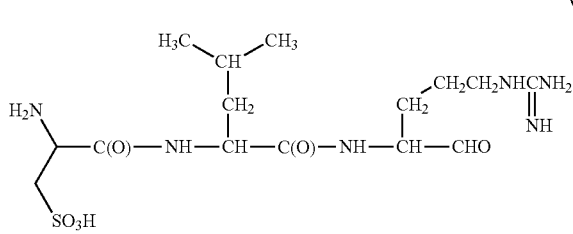

which is cysteic acid directly bonded to leucyl-arginal. Compound V is referred to herein as cysteyl-leucyl-arginal ("CLA"). Compound V can also exist as the pharmaceutically acceptable salt thereof.

In a related and preferred aspect, CLA can be synthesized as described in Experiment 1 below, and utilized in the form of a prodrug having the formula VI:

VI

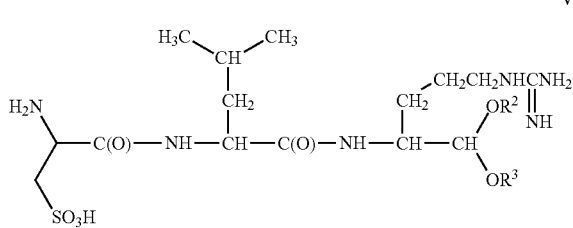

wherein $R^2$ and $R^3$ can be, independently, a branched- or straight-chain alkyl group having from 1 to 20 carbon atoms, or preferably a branched- or straight-chain alkyl group having from 1 to 3 carbon atoms, or preferably $R^2$ and $R^3$ are ethyl groups.

The Linker Groups

Alternatively, the carrier molecule and protease inhibitor can be indirectly bonded to one another via the use of a linker residue. A "linker residue," which is denoted as "L" in formulae I-III, is any compound that has at least one group that can form a covalent bond with the carrier molecule and at least one group that can form a covalent bond with the protease inhibitor.

In some embodiments, the linker group L can have up to 25 carbon atoms, or from 1 to 12, 1 to 6, or 2 to 4 carbon atoms. In related embodiments, the linker has the formula Z—$(CH_2)_m$—W, wherein W and Z are, independently, O, S, or $NR^1$, wherein $R^1$ is hydrogen or branched or straight chain alkyl, and m is from 1 to 12, 1 to 11, 1 to 10, 1 to 9, 1 to 8, 1 to 7, 1 to 6, 1 to 5, 1 to 4, 1 to 3, or 1 to 2. In a similar manner, the linker can be a polyalkylene group, a polyether group having the formula —(Z—$CH_2CH_2)_m$—W, wherein W and Z are independently selected from the group consisting of O, S, or NH and m is from 1, 2, or 3, or a polyamide group, a polyimino group, a polyester, an aryl group, or a polythioether group having two or more groups capable of reacting with the carrier molecule and protease inhibitor. It is contemplated that the linker can be of varying molecular weight. Examples of linker molecules include, but are not limited to, ε-aminocaproic acid, polyethyelene glycol, glutaraldehyde, and the like.

In some such embodiments, functional groups present on the carrier molecule and/or protease inhibitor can be chemically modified prior to direct or indirect bonding. For example, the terminal amino group of the leucyl residues of the leucyl argininal groups can be modified and/or replaced by various methods well known to those of ordinary skill in the chemical arts, or replaced by a carbon or heteroatom from the linker L, atom such as oxygen or sulfur, to give residues having the structures shown below:

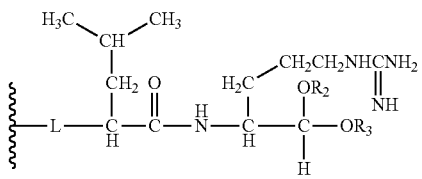

In some embodiments of the compounds of the invention, L is an "amino acid" in the broad sense that it comprises an organic residue having both an —NH— residue that is bonded to a carbon of the cysteic acid residue, and also a —C(O)— (carbonyl) residue analogous to that of a carboxylic acid, bonded to the organic residue and —NH— residue of the protease inhibitor residue Y. In many embodiments, these organic residues can have 1 to 20, 1 to 12, 1 to 6, or 1 to 4 carbon atoms. In some embodiments, L is a polypeptide residue, or a residue of a naturally or unnaturally occurring α-amino acid, including a naturally occurring α-amino acids selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine, or any of a wide variety of analogs of the naturally occurring amino acids that are readily commercially available from a number of commercial chemical supply houses, including Aldrich Chemical of Milwaukee Wis. For example, in some embodiments wherein L is an "amino acid", the L-Y residues could comprise the structures

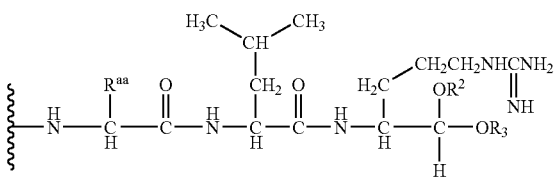

wherein $R^{aa}$ is selected from the group consisting of hydrogen, methyl, isopropyl, and isobutyl, and wherein $R^2$ and $R^3$ are independently selected from the group consisting of a branched or straight chained alkyl group having from 1 to 4 carbon atoms.

In a number of related embodiments, L is a residue of an unnatural or synthetic amino acid that can have a wide variety of structures. L can comprise a three-to seven-membered cycloalkyl or heterocyclic ring, such as for example compounds wherein L has the structure

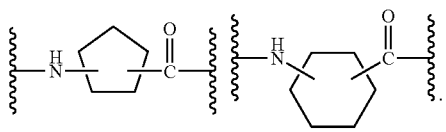

L may also comprise an aryl or heteroaryl ring, such as compounds wherein L has the structure

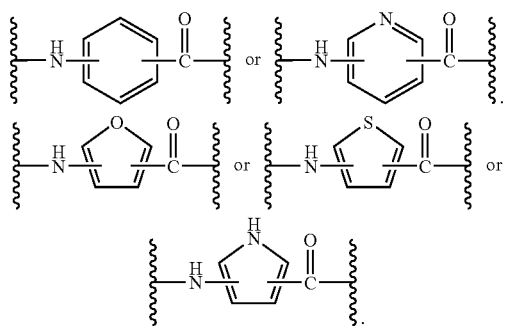

It is contemplated that the linker molecule can be covalently attached to the carrier molecule, the protease inhibitor, or both prior to linking the carrier molecule to the protease inhibitor. The techniques disclosed in U.S. Pat. Nos. 4,742,081; 4,866,040; 5,008,288; and 5,876,747 for directly or indirectly bonding a carrier molecule to a linker and/or a protease inhibitor, which are incorporated by reference in their entireties, can be used herein. In one aspect, the carrier molecule can be directly bonded to the protease inhibitor with the use of a carbodiimide. These sorts of synthetic techniques are illustrated herein in Experiment 1 and FIG. 1a below. For example, cysteic acid can be reacted with the protease inhibitor in the presence of a carbodiimide to form a new covalent bond.

Figure 1B:
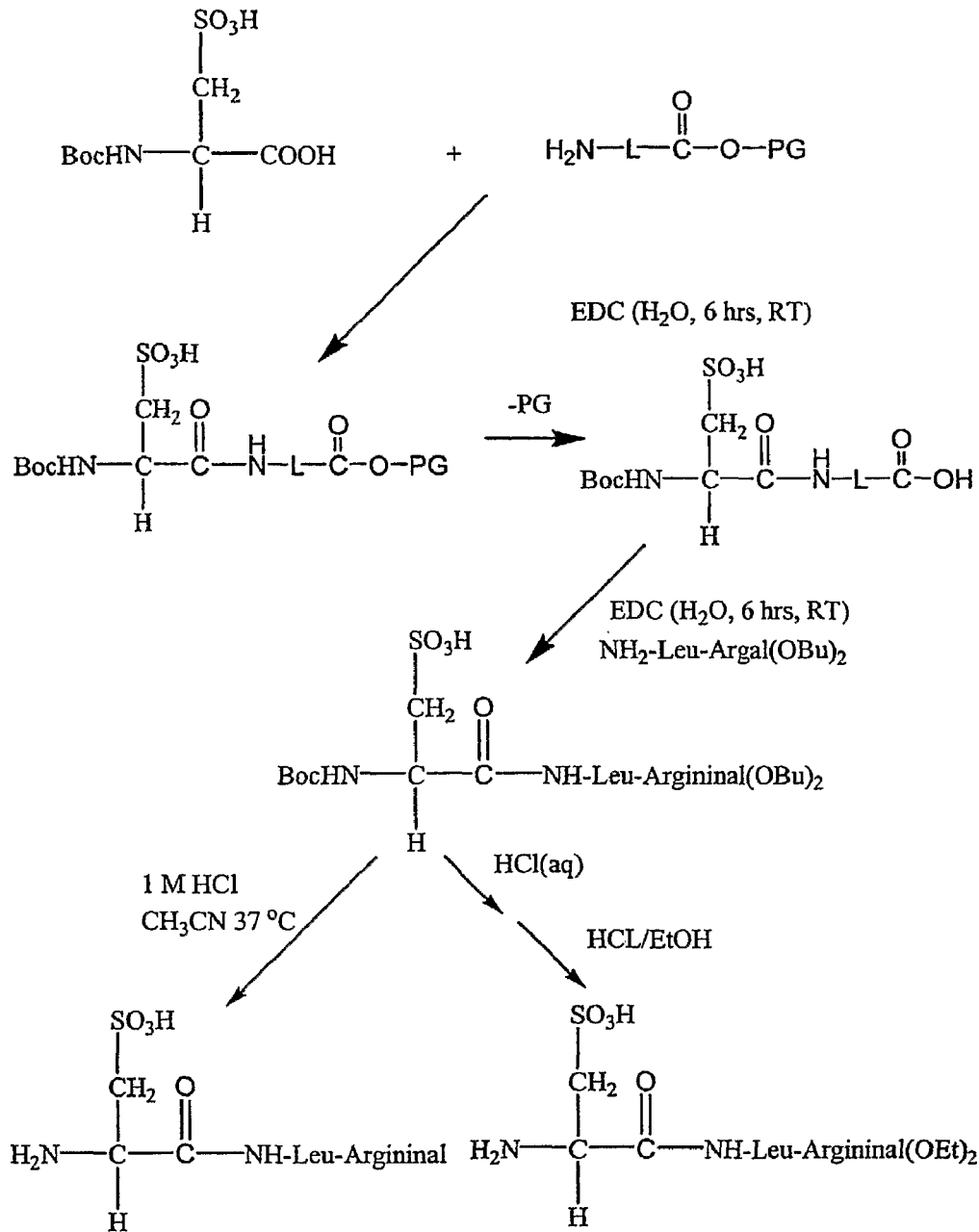
FIG. 1b shows a generic synthetic method for making linked cysteic acid/leucyl-argininal calpain inhibitor compounds
Figure 1C:
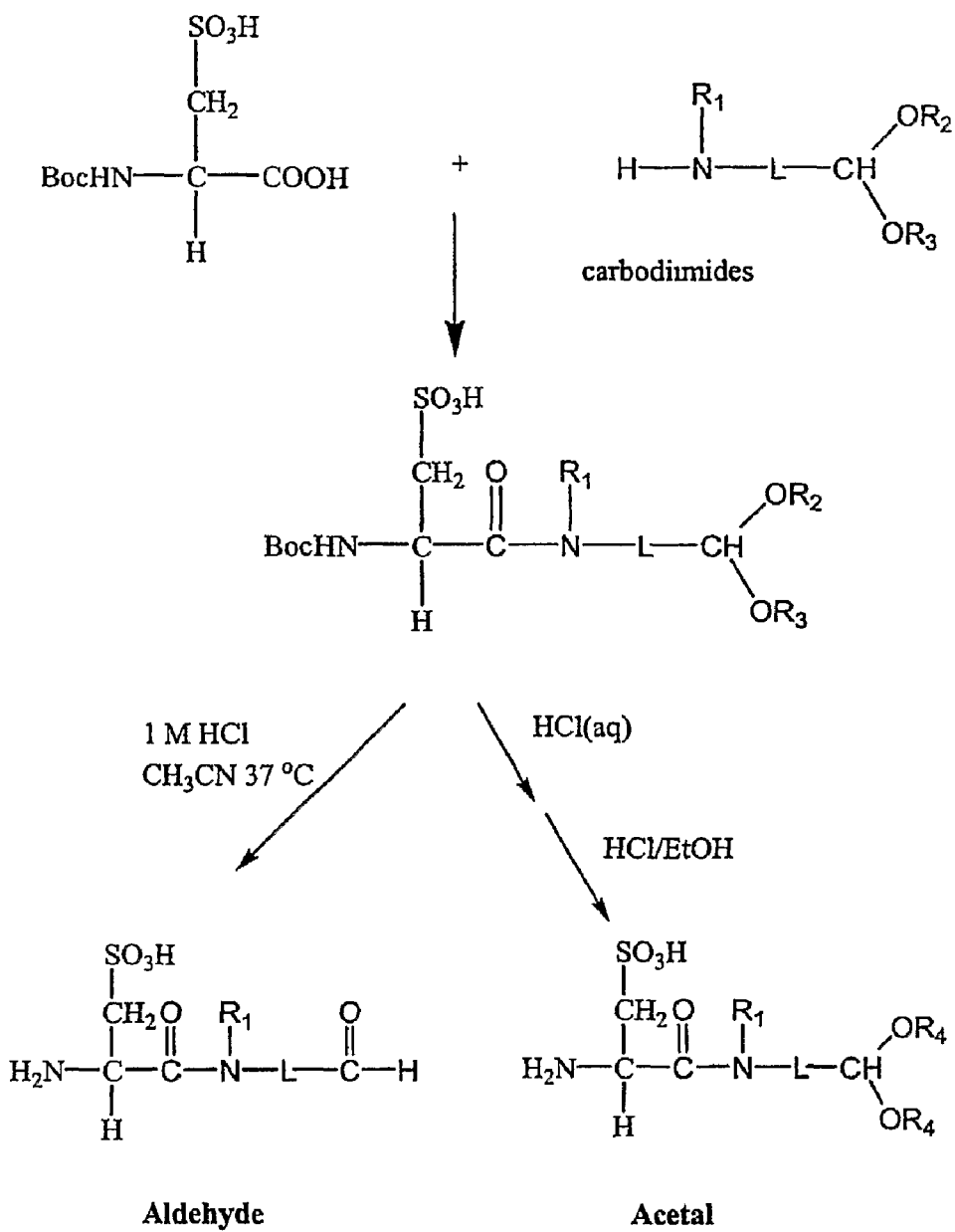
FIG. 1c shows a generic synthetic method for making linked cysteic acid/aldehyde calpain inhibitor compounds.

In related embodiments, the synthesis of compounds of the invention comprising linker groups connecting the cysteic acid residues and the protease inhibitors can be readily carried out in analogy to and using the methods well known to those of ordinary skill in the art for the synthesis of peptides, such as the use of Boc or Fmoc amine protecting groups, in conjunction with the use of carbodiimides as reagents to activate the carboxylic acid groups, so as allow repeated additions of amino acid residues to the chain. FIGS. 1b and 1c illustrate such generic synthetic methods, and it should be noted that the carbodiimide activation procedure for the carboxylic acids is well known to also be applicable to formation of carboxylic acid esters if the activated carboxylic acid is condensed with an organic alcohol.

The compounds having the formulas I-III typically comprise carbon atoms that are asymmetric, i.e. they can be optically active, and each of the optically active centers can comprise the substantially pure L- or D enantiomers, or any mixture thereof, including a 50:50 mixture of the enantiomers, so as to form a racemic mixture. The term "substantially pure" with respect to the L- or D enantiomers refers to greater than 95%, greater than 97%, greater than 98%, greater than 99%, greater than 99.5%, or 100% of one enantiomer with respect to the other enantiomer. In many embodiments of the invention, the linker or protease inhibitor can comprise natural α-amino acids whose α carbon atom in the "L" configuration.

Purification of the compound can be accomplished using techniques well known to those of ordinary skill in the art, such as chromatography, crystallization, etc.

Pharmaceutically Acceptable Salts

Compounds having the formula VI can also exist as the pharmaceutically acceptable salt thereof.

Any of the compounds described herein can be the pharmaceutically-acceptable salt thereof. In one aspect, pharmaceutically-acceptable salts are prepared by treating the free acid with an appropriate amount of a pharmaceutically-acceptable base. For example, one or more hydrogen atoms of the $SO_3H$ group can be removed with a base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like.

In another aspect, if the compound possesses a basic group, it can be protonated with an acid such as, for example, HCl or $H_2SO_4$, to produce the cationic salt. For example, the techniques disclosed in U.S. Pat. No. 5,436,229 for producing the sulfate salts of argininal aldehydes, which is incorporated by reference in its entirety, can be used herein. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

It is well known to those of ordinary skill in the art that amino acid, peptide, and protein compounds comprise both acidic groups and basic groups, and in practice they often actually exist in the form of internal salts, especially zwitterionic salts. As a result, in many embodiments of the compounds of the inventions, the compounds are actually made, stored, and used in the form of pharmaceutically acceptable salts that have one or more of the following features a) the —$NH_2$ residue is present in the form of —$NH_3^+$, b) the —$SO_3H$ residue is present in the form of $SO_3^-$, and/or c) the argininal residue is present in a form having the structure

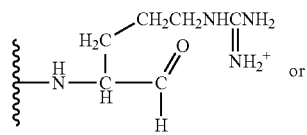

-continued

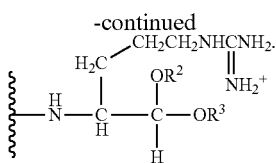

To further exemplify, one of the preferred compounds of the invention is cysteyl-leucyl argininal ("CLA") which is often written as having the first structure shown in the drawing below, even though one of ordinary skill in the art would recognize that the CLA compound predominately exists (at neutral pH) in the form of the zwitterionic salt shown at the bottom of the drawing.

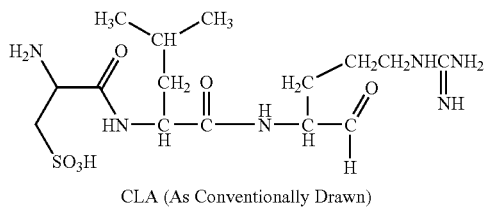

CLA (As Conventionally Drawn)

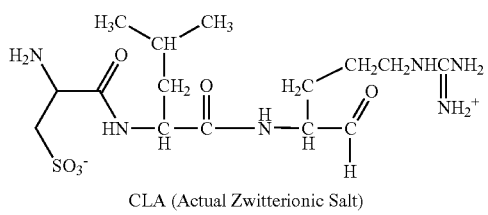

CLA (Actual Zwitterionic Salt)

Moreover, for purposes of ease of synthesis, purification, formulation, and absorption, many of the compounds of the invention are further neutralized with a pharmaceutically acceptable acid, to form a pharmaceutically acceptable salt comprising a cation having structures analogous to the CLA salt shown below:

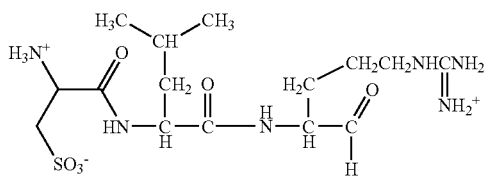

wherein the CLA is present in the form of a zwitterionic monocation, and hence the pharmaceutically acceptable salt must further contain one or more pharmaceutically acceptable anions. A wide variety of such pharmaceutically acceptable anions are known in the art, as exemplified by a fluoride, chloride, bromide, iodide, sulfate, nitrate, phosphate, hydrogen phosphate, dihydrogen phosphate, carbonate, bicarbonate, formate, acetate, propionate, lactate, fumarate, succinate, or an anion derived from a fatty carboxylic acid. For example, if the active compound comprising the amine group is oxidatively unstable, it can be prepared as its salt form in order to increase oxidative and thermal stability in dry form (e.g., powder).

In some embodiments, the invention relates to a compound having the formula

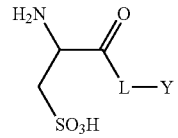

wherein L is a residue of a linker that is not —NH—; and
Y comprises a residue of a calpain inhibitor or a prodrug thereof;
or a pharmaceutically-acceptable salt thereof.
In many such embodiments, Y is a residue of leucyl-argininal.

II. Pharmaceutical Compositions and Kits
Pharmaceutical Compositions

In one aspect, any one or more of the compounds described above, or their pharmaceutically acceptable salts, can be combined with at least one pharmaceutically-acceptable carrier to produce a pharmaceutical composition. Thus another embodiment is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the composition and not overly deleterious to the recipient thereof.

Pharmaceutically-acceptable carriers are known to those skilled in the art. These most typically would be standard carriers for administration to humans, including solutions such as sterile water, saline, and buffered solutions at physiological pH, and may include at least small amounts of several pharmaceutically acceptable solvents, such as ethanol, propylene glycol, dimethyl sulfoxide, and the like.

Molecules intended for pharmaceutical delivery may be formulated in a pharmaceutical composition. Pharmaceutical compositions may include well known thickeners (such as alkylated or hydroxyalkylated celluloses, dextrans, gums, alginates, pectins, and the like), diluents, buffers, preservatives, surface active agents and the like in addition to the active compounds of choice. Pharmaceutical compositions may also include one or more active ingredients such as antimicrobial agents, anti-inflammatory agents, anesthetics, and the like.

Pharmaceutical compositions suitable for oral administration can be presented and administered as discrete unit dosage forms such as hard or soft gelatin capsules, cachets or tablets each containing a predetermined amount of the active ingredient; as a powder or as granules; as a solution, a suspension or as an emulsion. The active ingredient can also be presented and administered as a bolus, electuary or paste. Tablets and capsules for oral administration can contain conventional excipients such as binding agents, fillers, lubricants, disintegrants, or wetting agents. The tablets can be coated according to methods well known in the art., e.g., with enteric coatings.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof. The pharmaceutical compositions according to the invention can also contain other adjuvants such as flavorings, coloring, antimicrobial agents, or preservatives.

The pharmaceutical compositions can be prepared using techniques known in the art. In one aspect, the composition is prepared by mixing one or more of the compounds of the invention with one or more pharmaceutically-acceptable carriers. Depending upon the components to be mixed, there may or may not be a chemical or physical interaction between two or more components.

Kits

Described herein are kits that can be very useful for delivering and/or administering the compounds of the invention to a subject for the treatment or prevention of a one or more of the neurological disorders mentioned herein. In one aspect, described herein is a kit for treating or preventing a neurological disorder in a subject comprising:
a. an effective amount of a prodrug of a compound, wherein the compound comprises a carrier molecule and a protease inhibitor, wherein the carrier molecule is directly or indirectly bonded to one or more protease inhibitors, and
b. an activator, wherein the activator converts the prodrug to the active form of the compound.

It is hereby contemplated that acetal prodrugs of any of the compounds described can be used in the kit. In one such aspect, a neutralizing base can be added to the mixture of prodrug and activator, to reduce the acidity of the activated drug prior to administration. In another aspect, acetal prodrugs of any one or more of the compounds encompasses within formulas I-V, or any of their subgenuses or species, can be used as the acetal prodrug in the kit.

The activator used in the kit is a compound or mixture of compounds that converts the acetal prodrug to the active aldehyde form of the compound. The selection of the activator will vary depending upon the prodrug (i.e., the nature of the protecting group, the quantity and nature of any other components of the pharmaceutical compositions). Examples of activators include, but are not limited to, inorganic acids such as, for example, hydrochloric acid, sulfuric acid, nitric acid, phosphoric acid, organic acids such as, for example, maleic, oxalic, citric, tartaric, and acetic acids. Hydrochloric, sulfuric and phosphoric acids can be preferred activator compounds. In addition, activators may include substances that act as catalysts for activation such as, for example, enzymes, metals, salts, polymers, detergents, and zeolites. Examples of enzymes useful herein include hydrolases, esterases, glycosidases, glycanases, proteases, lipid-metabolizing enzymes, oxidases, and cytochrome P450 enzymes.

Depending upon the activator that is used, a neutralizing agent can be an optional component of the kit. The neutralizing agent is any compound or mixture of compounds that renders the activating agent safe for consumption or administration to a subject after the acetal prodrug has been converted to the active aldehyde compound. For example, a basic neutralizing agent can neutralize an acidic activator inactive after the acetal prodrug has been converted to the active aldehyde compound or, in the alternative, convert the activator to a compound that is not harmful to a subject. The neutralizing agent will vary depending upon the selection of the activator. For example, when the activator is an acid, the neutralizing agent can be a strong inorganic base such as sodium hydroxide or a weak base such as dibasic sodium phosphate. In another aspect, once the activator has converted the prodrug to the active compound, the mixture can be diluted in a beverage to neutralize any remaining activator.

Depending upon the end-use of the kit, the prodrug, activator, and neutralizing agent can exist as solids or solutions. For example, it is contemplated that the prodrug be prepared or stored in a solid or gel form, or aqueous solution, and the activator is stored in aqueous solution. Alternatively, it is possible that the prodrug and the activator are both in solid form together or separately. In this aspect, water alone or in combination with other components can be added to the solid mixture. For example, sterile water, saline, and buffered solutions at physiological pH can be used to store the prodrug or activate the prodrug with the activator.

Depending upon the selection of the activator and the prodrug, it may be desirable to gently heat the prodrug and the activator upon mixing in order to expedite the conversion of the prodrug to the active compound. In one aspect, the kit further comprises a heating device. In one aspect, the heating device can be a Peltier block modified to hold a vial containing a mixture of the prodrug and activator. It is also contemplated that the kit can comprise a cooling device to cool the solution of the active compound if the solution was heated by the heating device.

In one example of the application of kits to the administration of the compounds of the inventions, the activator is HCl or phosphoric acid, and the acetal prodrug has the formula VI:

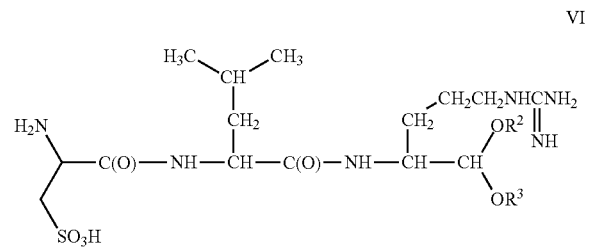

or the acetal prodrug is in the form of a pharmaceutically acceptable salt comprising a cation having the structure

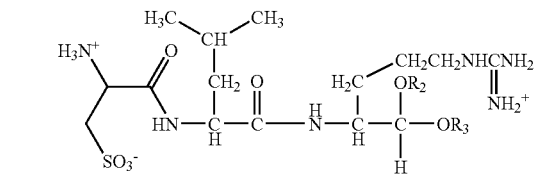

wherein the salt also comprises one or more pharmaceutically acceptable anions.

The prodrug and activator can be mixed in any order. The duration of the mixing can vary depending upon the prodrug and activator selected as well as the relative amount of activator to prodrug. The duration of admixing is sufficient to convert the prodrug substantially (i.e., greater than 80%, greater than 85%, greater than 90%, greater than 95%, or greater than 99%) or completely to the active compound. Once the activator and the acetal prodrug are mixed to produce the active compound, the active compound can be administered to the subject by a variety of techniques as will be described below. Methods for delivering the compounds described herein, which include the active compound produced from the kits, will also be described below.

II. Methods of Use

Therapeutic Uses

In one aspect, disclosed are methods for using the compounds or pharmaceutically acceptable salts or compositions thereof, or kits comprising the compounds or pharmaceutically acceptable salts or compositions thereof, for preventing or treating a neurologic disease in a subject, animal, mammal, or human, which involves administering an effective amount of any of the compounds described herein to a subject diagnosed with or in need of such treatment or prevention of the recited neurological diseases or injuries. Additionally, any of the compounds of the invention described herein can be used to manufacture a medicament for the treatment of the disclosed neurological diseases or injuries.

Examples of neurologic diseases that can be treated or prevented by the methods described herein include, but are not limited to, amyotrophic lateral sclerosis, Alzheimer's disease, multiple sclerosis, Huntington's disease, Parkinson's disease, spinocerebellar atrophies, and inflammatory demyelinating neuropathy. In one preferred embodiment, the neurologic disease is multiple sclerosis.

In one aspect, described herein are methods for treating or preventing a neurologic disease, an otologic disease, or an ophthalmologic disease in a subject diagnosed with such comprising administering to the subject an effective amount of the compound having the formula:

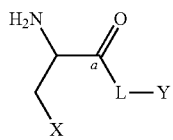

wherein L is a residue of an optional linker;
X is SO$_3$H or SO$_2$H; and
Y comprises a residue of a protease inhibitor;
or the pharmaceutically-acceptable salt thereof or the prodrug thereof,
wherein when L is not present, Y is bonded to a carbon a.

Any of the protease inhibitors, linkers, and combinations thereof described above can be used in the methods described above or below.

In one aspect, compounds having the formula V and VI can be used in the treatment or prevention of a neurologic disease, an otologic disease, or an ophthalmologic disease.

In other related aspects, the invention relates to a method for treating or preventing multiple sclerosis comprising administering to an animal subject, in an amount effective to treat or prevent multiple sclerosis, one or more compounds having the structure

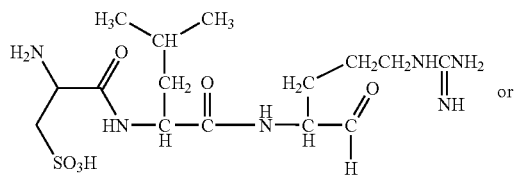

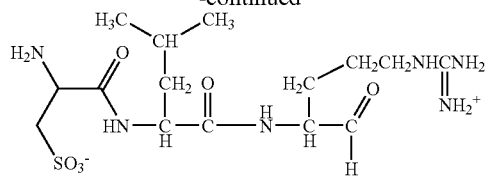

or a pharmaceutically acceptable salt thereof.

In other related aspects, the invention relates to methods for treating or preventing multiple sclerosis comprising administering to an animal subject, in an amount effective to treat or prevent multiple sclerosis, one or more compounds having the formula

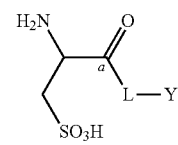

wherein L is an optional linker residue comprising up to 25 carbon atoms; Y is an acetal prodrug of a leucyl-argininal residue; wherein when L is not present and Y is bonded to carbon a; or a pharmaceutically-acceptable salt thereof.

In other related aspects, the invention relates to methods for treating or preventing an otologic disease in a subject diagnosed with the otologic disease comprising administering to the subject an effective amount of the compound having the formula IV

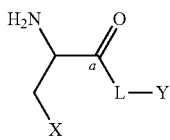

wherein L is a residue of an optional linker;
X is SO$_3$H or SO$_2$H; and
Y comprises a residue of a protease inhibitor;
or the pharmaceutically-acceptable salt thereof or the prodrug thereof,
wherein when L is not present and Y is bonded to carbon a.

In many such embodiments, the otologic disease is acoustic trauma, or antibiotic induced ototoxicity.

In other related aspects, the invention relates to methods for treating or preventing a degenerative ophthalmologic disease in a subject diagnosed with the ophthalmologic disease comprising administering to the subject an effective amount of the compound having the formula:

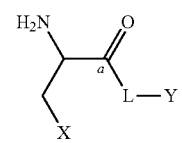

wherein L is a residue of an optional linker;
X is SO$_3$H or SO$_2$H; and
Y comprises a residue of a protease inhibitor;
or the pharmaceutically-acceptable salt thereof or the prodrug thereof,
wherein when L is not present and Y is bonded to carbon a.

In some related embodiments, the ophthalmologic disease is retinal degeneration, retinal injury, macular degeneration, or retinitis pigmentosa, glaucoma, or cataracts.

In one aspect, described herein is a method for treating or preventing multiple sclerosis in a subject diagnosed with multiple sclerosis comprising administering to the subject an effective amount of cysteyl-leucyl-argininal or a prodrug thereof. In another aspect, described herein is a method for treating or preventing retinal degeneration in a subject diagnosed with retinal degeneration comprising administering to the subject an effective amount of cysteyl-leucyl-argininal (formula V) or a prodrug thereof. In a further aspect, described herein is a method for treating or preventing macular degeneration in a subject diagnosed with macular degeneration comprising administering to the subject an effective amount of cysteyl-leucyl-argininal or a prodrug thereof.

In another aspect, the compounds described herein can inhibit calpain activity in a subject. Calpains are a family of $Ca^{+2}$ activated intracellular proteases whose activity is accelerated when abnormal amounts of $Ca^{+2}$ enter the cell by virtue of increased membrane permeability as a result of some traumatic or ischemic event and/or a genetic defect. The trigger which activates calpain is $Ca^{+2}$ ions leaking into cells and/or released locally from intracellular stores, where the levels are generally very low. Calpain is one of a relatively small family of cysteine proteases, which are active in promoting programmed cell death or apoptosis. It has been implicated in the initiation of both necrotic and apoptotic cell death. Calpain has also been implicated in the neurotoxicity that follows spinal cord injury. In one aspect, compounds having the formula IV can be used to inhibit calpain activity in white matter of a subject comprising administering a compound having the formula IV to the subject. In another aspect, compounds having the formula V and VI can be used to inhibit calpain activity in neural tissue such as, for example, the white matter of a subject.

In another aspect, described herein are methods for reducing or preventing myelin degeneration in a subject comprising administering to the subject an effective amount of the compound having the formula IV. It has been suggested that calpain expression and activity is involved in demyelinating diseases such as, for example multiple sclerosis. In one aspect, compounds having the formula V and VI can be used to reduce or prevent myelin degradation.

In one aspect, described herein is a method for treating or preventing multiple sclerosis in a subject diagnosed with multiple sclerosis comprising administering to the subject an effective amount of cysteyl-leucyl-argininal or a prodrug thereof. In another aspect, described herein is a method for treating or preventing retinal degeneration in a subject diagnosed with retinal degeneration comprising administering to the subject an effective amount of cysteyl-leucyl-argininal or a prodrug thereof. In a further aspect, described herein is a method for treating or preventing macular degeneration in a subject diagnosed with macular degeneration comprising administering to the subject an effective amount of cysteyl-leucyl-argininal or a prodrug thereof.

In one aspect, described herein is a method for treating or preventing a neurologic disease in a subject diagnosed with the neurologic disease comprising administering to the subject an effective amount of cysteyl-leucyl-argininal or a prodrug thereof. In another aspect, described herein is a method for inhibiting calpain activity in nervous tissue in a subject comprising administering to the subject an effective amount of cysteyl-leucyl-argininal or a prodrug thereof. In a further aspect, described herein is a method for reducing or preventing myelin degeneration in a subject comprising administering to the subject an effective amount of cysteyl-leucyl-argininal or a prodrug thereof.

In one aspect, any of the compounds described herein can be used as a therapeutic. In one aspect, described herein is a method for therapeutically treating a subject comprising administering to the subject an effective amount of the compound having the formula IV. The term "therapeutic" and "therapeutically" as used herein means curing or healing a subject who is suffering from a disease or injury. Besides neurologic, otologic, and ophthalmologic diseases, the compounds described herein can be used as a therapeutic in a number of other diseases or injuries. Calpain activation has been associated with a variety of diseases and injuries such as, for example, stroke, a spinal cord contusion, a traumatic brain injury, excitotoxicity, and ischemia (73-87), and the compounds described herein can be used as a therapeutic for these diseases and injuries. In one aspect, cysteyl-leucyl-argininal can be used as a therapeutic.

Administration of the Compounds and Compositions

As used throughout, administration of any one or more of the compounds described herein can be mixed with and used in conjunction with other therapeutic agents. Thus, the compound can be administered alone or in combination with one or more therapeutic agents. For example, a subject can be treated with a compound alone, or in combination with chemotherapeutic agents, antibodies, antivirals, steroidal and non-steroidal anti-inflammatories, conventional immunotherapeutic agents, cytokines, chemokines, and/or growth factors. Combinations may be administered either concomitantly (e.g., as a mixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents.

The compounds can be administered in a number of ways depending on whether local or systemic treatment is desired, and on the area to be treated. Administration may be topically (including ophthalmically, vaginally, rectally, intranasally), orally, by swallowing or inhalation, or parenterally, for example by intravenous drip, subcutaneous, intracutaneous, intraperitoneal or intramuscular injection. In one aspect, the compounds can be delivered intrathecally. It is also contemplated that the compounds can be administered transdermally via, for example, a patch or ionotophoresis. The disclosed compounds can be administered intravenously, intraperitoneally, intramuscularly, subcutaneously, intracavity, intraocularly (e.g., intravitreally), transdermally, intracisternally, intraventricularly, intratracheally, extracorporeally, or topically (e.g., topical intranasal administration or administration by inhalant). As used herein, "topical intranasal administration" means delivery of the compositions into the nose and nasal passages through one or both of the nares and can comprise delivery by a spraying mechanism. The latter can be effective when a large number of subjects are to be treated simultaneously. Administration of the compositions by inhalant can be through the nose or mouth via delivery by a spraying mechanism or droplet mechanism. Delivery can also be directly to any area of the respiratory system (e.g., lungs) via intubation.

In one aspect, when the compound is a prodrug, the compound can be administered orally so that after ingestion, the acidic conditions present in the stomach can at least partially convert the acetal prodrug to the active aldehyde form of the compound before absorption of the drug, but substantial evidence indicates that the acetal prodrug compounds of the invention can be directly absorbed in the intestinal tract and into serum and cells prior to the conversion of the acetal group to the aldehyde form, and that the conversion from acetal to aldehyde can occur in-vivo and in-situ in the targeted nervous tissues.

Parenteral administration of the compound, if used, is generally characterized by injection. Injectables can be prepared in conventional forms, either as liquid solutions or suspensions, solid forms suitable for solution of suspension in liquid prior to injection, or as emulsions. Alternatively, parenteral administration can involve the use of a slow release or sustained release system such that a constant dosage is maintained.

The exact amount of the compounds described herein required will vary from subject to subject, depending on the species, age, weight and general condition of the subject, the severity of the disorder being treated, the particular neurologic disorder to be targeted, its mode of administration and the like. Thus, it is not possible to specify an exact amount for every compound. However, an appropriate amount can be determined by one of ordinary skill in the art using only routine experimentation given the teachings herein. The time at which the compounds can be administered will also vary depending upon the subject, the disorder, mode of administration, etc. The compound can be administered to the subject prior to the onset of the neurologic, otologic, or ophthalmologic disorder or during a time when the subject is experiencing symptoms of the disorder. The compound can be administered over several weeks or months at varying intervals depending upon the subject and disorder to be treated. In one aspect, any of the compounds described herein can be administered to treat a neurologic, otologic, or ophthalmologic disease or used as a therapeutic at a dosage from 0.01 mg/kg to 1,000 mg/kg. In another aspect, the lower endpoint of the dosage is 0.01, 0.05, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10.0, 15.0, 20.0, 25.0, 30.0, 35.0, 40.0, 45.0, 50.0, 60.0, 70.0, 80.0, 90.0, 100.0, 150.0, 200.0, 250.0, 300.0, 350.0, 400.0, 450.0, 500.0, 600.0, 700.0, 800.0, or 900.0 mg/kg, and the upper endpoint of the dosage is 1.0, 2.0. 3.0. 4.0. 5.0, 6.0, 7.0, 8.0, 9.0, 10.0, 15.0, 20.0, 25.0, 30.0, 40.0, 50.0, 60.0, 70.0, 80.0, 90.0, 100.0, 150.0, 200.0, 250.0, 300.0, 350.0, 400.0, 450.0, 500.0, 550.0, 600.0, 650.0, 700.0, 750.0, 800.0, 850.0, 900.0, 950.0, or 1,000.0 mg/kg, where any lower endpoint can be used with any upper endpoint, where the lower endpoint is less than the upper endpoint. In another aspect, the dosage is from 1 to 10 mg/kg or 1 to 5 mg/kg.

The desired dose can conveniently be presented in a single dose per day or week, or as divided doses administered at appropriate intervals, for example, as two, three, four or more sub-doses per day. The sub-dose itself can be further divided, e.g., into a number of discrete loosely spaced administrations; such as multiple inhalations from an insufflator or by application of a plurality of drops into the eye.

The pharmaceutical composition may be administered in a number of ways depending on whether local or systemic treatment is desired, and on the area to be treated. Administration may be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

It will be appreciated that the actual preferred amounts of active compound in a specified case will vary according to the specific compound being utilized, the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (2004).

In another aspect, any of the compounds described herein can be administered to a subject with the use of a liposome. In one aspect, the carrier molecule and/or protease inhibitor of the compound can be covalently attached to the liposome by reacting the carrier molecule and/or protease inhibitor with the phospholipid used to produce the liposome. In another aspect, the compounds described herein can be enclosed within the inner volume of the liposome and not covalently attached to the liposome. Examples of liposomes useful herein include, but are not limited to, conventional liposomes, long-circulating liposomes, immunoliposomes, and cationic liposomes. The methods disclosed in U.S. Pat. Nos. 4,866,040; 5,008,288; and 5,876,747, which are incorporated by reference, can be used to produce liposome formulations with the compounds described herein. In another aspect, the compounds described herein can be delivered to a subject via micelles, nanoparticles, microspheres, and lipoproteins.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Synthesis of cysteyl-leucyl-argininal (CLA) and its acetals

FIG. 1 shows the synthesis of cysteyl-leucyl-argininal (CLA) and the ethyl acetal of CLA. $NH_2$-Leu-Argal(OBu)$_2$ was prepared using techniques described in U.S. Pat. No. 5,008,288. All other starting materials including cysteic acid are commercially available.

II. Induction of EAE and Treatment with CLA

Experiment 1: CLA-Treatment was Started at the Time of Immunization with MOG aa35-55 in Order to Observe a Maximum Effect.

Figure 2:
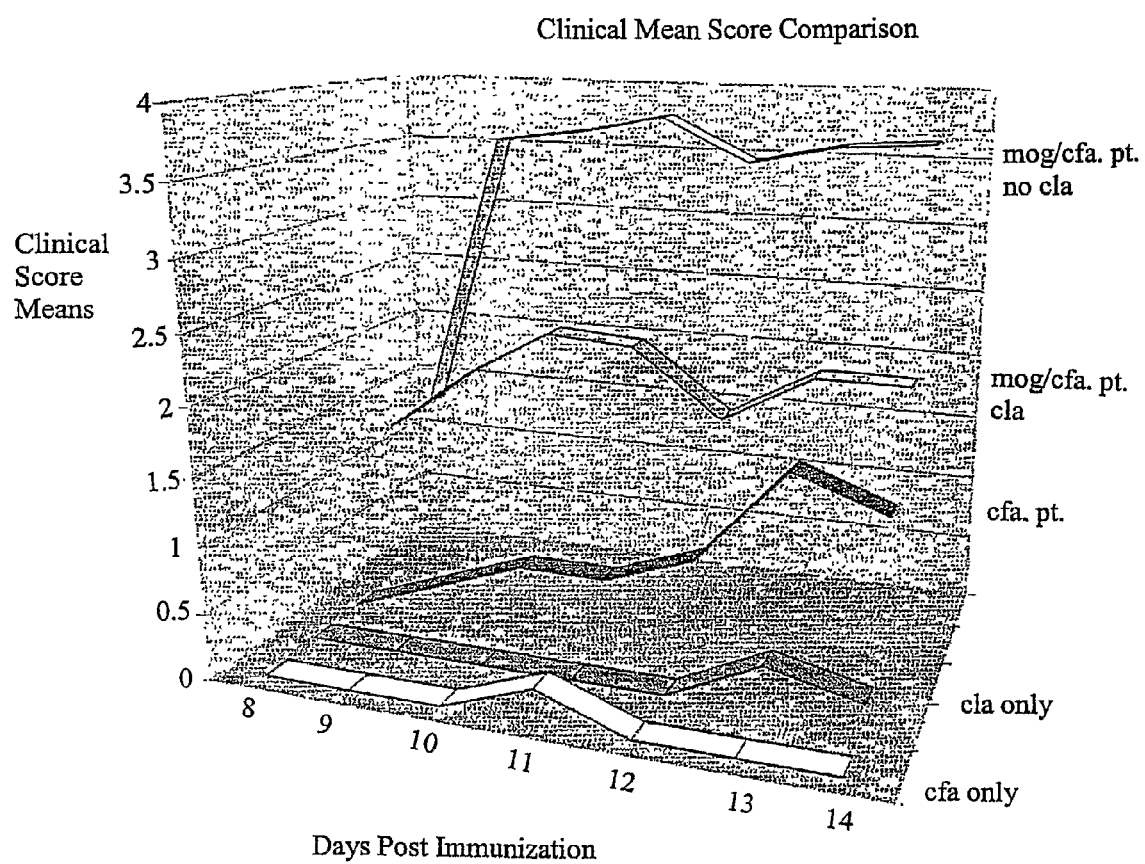
FIG. 2 shows the average clinical scores (ACS) of all mice over time.
Figure 3:
FIG. 3 shows the cellular infiltration in spinal cord white matter.
Figure 3:
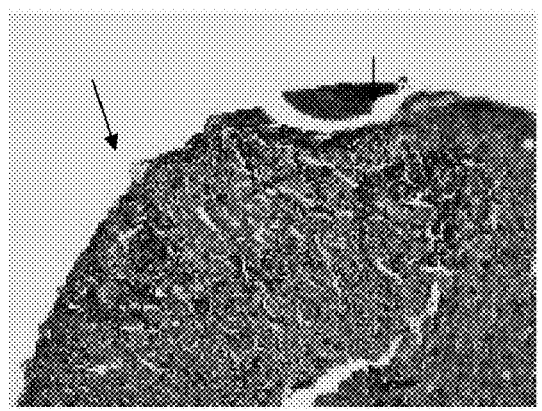
Figure 3:

To induce EAE, 7-8 week-old female C57BL/6J mice (Jackson Laboratories, Bar Harbor, Md.) were used. Animals were housed according to IACUC regulations in an AAALAC certified facility. Each was injected subcutaneously (s.c.) at two sites on the flanks with 300 μg of myelin oligodendrocyte glycoprotein (MOG) peptide 35-55 in Complete Freund's Adjuvant (CFA) twice with a one week interval between injections, as previously reported (14). Pertussis toxin (PT) was given intraperitoneally on days 0 and 2 post-immunization. CLA was administered to 12 MOG/CFA immunized mice, i.p. at an initial dose of one mg/mouse, starting on the day of the second immunization, followed by 0.5 mg/mouse/day until the end of the experiment, which lasted 19 days. The remaining 12 mice received CLA only, CFA only, and CFA and PT only and served as controls (FIG. 2).

Clinical evaluation: Mice were evaluated daily for clinical signs of disease for up to 19 days after inoculation. Clinical severity was assessed on a scale of 0-6 as follows:

0⇒no abnormality

1⇒mild hind limb weakness (some difficulty righting themselves when turned on their backs), sometimes associated with a weak or floppy tail.

2⇒moderate hind limb weakness associated with a floppy tail.

3⇒paralysis of hind limbs, sometimes more marked on one side, but no forelimb weakness.

4⇒hind leg paralysis accompanied by forelimb weakness.

5⇒quadriplegia; paralysis of both hind limbs and forelimbs.

6⇒moribund or death.

Scores of asymptomatic mice (score=0) were included in the calculation of the daily mean clinical score for each group.

Results

The data were plotted as the daily average clinical scores (ACS) for all mice in a particular treatment group or in a control group. The ACS of B6 mice induced with EAE was substantially reduced with the CLA treatment. The ACS of untreated animals was 3.28 versus a score of 1.86 in CLA-treated mice. The results were statistically significant (τ-test p=0.0041), and are presented in FIG. 2: a severe acute clinical EAE was induced in MOG/CFA inoculated mice (top line), and a significant reduction in clinical EAE was observed in CLA-treated MOG/CFA mice. CLA only or CFA/CLA had no effect on the mice. One mouse showed some signs of weakness when inoculated with CFA/PT.

Experiment 2: Histological Studies.

Hematoxylin and Eosin Staining (H&E): H&E staining was used to show cellular infiltration of spinal cord white matter in mice with acute EAE in comparison with other groups of CFA control and CLA-treated EAE mice, as previously described (14). All staining was performed on tissues that were collected at the end of the experiment. In FIG. 3, 6-10 μm tissue sections were prepared from spinal cords of all mice at the end of the experiment. These tissues were stained with H&E to show inflammatory infiltration (indicated by arrows). A: CFA control; B: MOG/CFA immunized; C: MOG/CFA immunized and CLA-treated. 20× magnification.

Spinal cord tissues from untreated EAE mice showed massive cellular infiltration and perivascular cuffing (FIG. 3B, see arrows). The inflammatory infiltration was distributed throughout the white matter. There was minimal inflammatory infiltrate in tissues of CFA control mice (FIG. 3A), and the tissues from CLA-treated EAE mice showed moderate cellular infiltration and perivascular cuffing (FIG. 3C). The cellular infiltration and perivascular cuffing in the EAE mice correlated with their severe clinical symptoms of disease.

Figure 4:
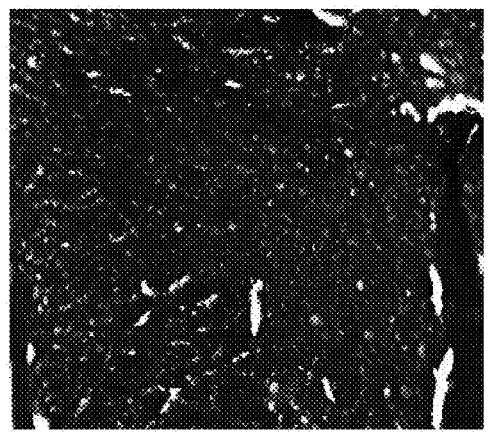
FIG. 4 shows the demyelination in the spinal cord white matter of mice.
Figure 4:
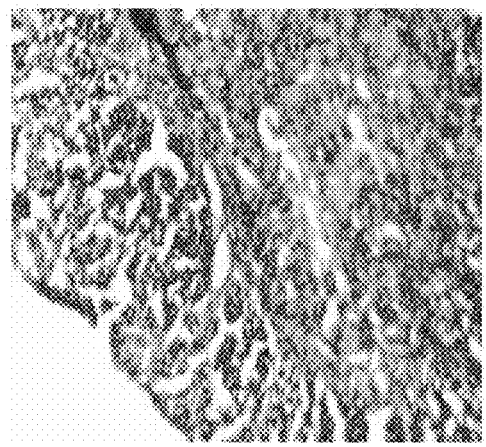
Figure 4:
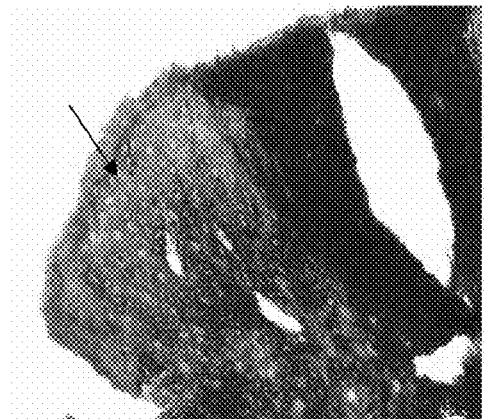

Luxol Fast Blue (LFB) Staining of Spinal Cord Tissues: This staining method, which identifies changes in myelin content of CNS tissues, was performed as previously described (39). Six-10 μm tissue sections were prepared from the lumbar spinal cords of all mice at the end of the experiment. The sections were stained with LFB and counterstained with eosin and cresyl violet to observe changes in the myelin content of the control and treatment groups: A: CFA control; B: MOG/CFA immunized: C; MOG/CFA immunized and CLA-treated. 20× magnification. All myelin containing regions stain blue. Large demyelinated regions devoid of blue-stained myelin (white regions in FIG. 4B) were observed in the white matter of the lumbar sections of spinal cord from MOG/CFA immunized mice. Intense blue stained myelin was observed in the spinal cord tissues of CFA control mice (FIG. 4A). Spinal cords of CLA-treated EAE mice had fewer areas of demyelination (i.e., fewer white regions) (FIG. 4C, see arrow).

Figure 5:
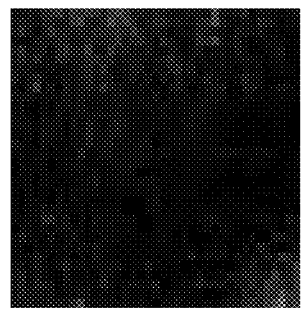
FIG. 5 shows single and double immunofluorescent staining of spinal cord white matter from all mice.
Figure 5:
Figure 5:
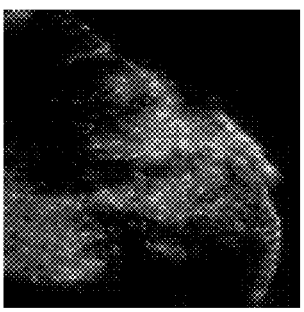
Figure 5:
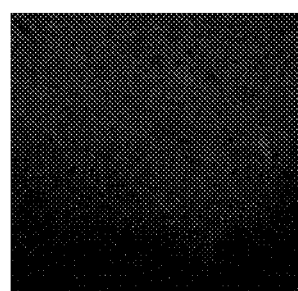
Figure 5:
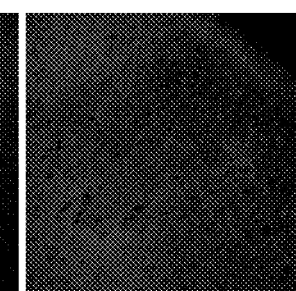
Figure 5:
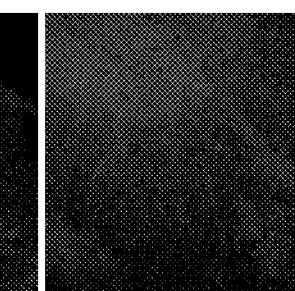
Figure 5:
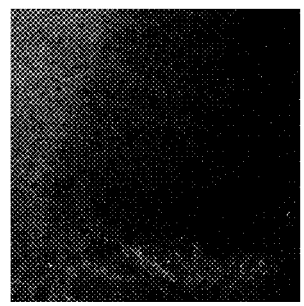
Figure 5:
Figure 5:
Figure 6:
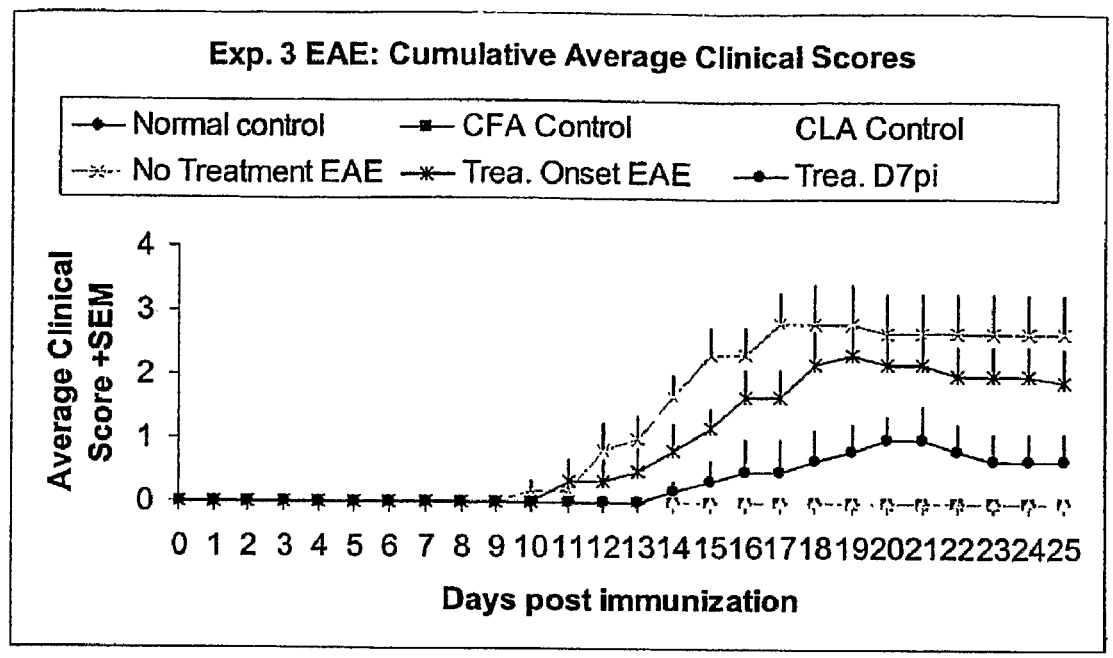
FIG. 6 shows the average clinical scores (ACS) of all mice over time.
Figure 7:
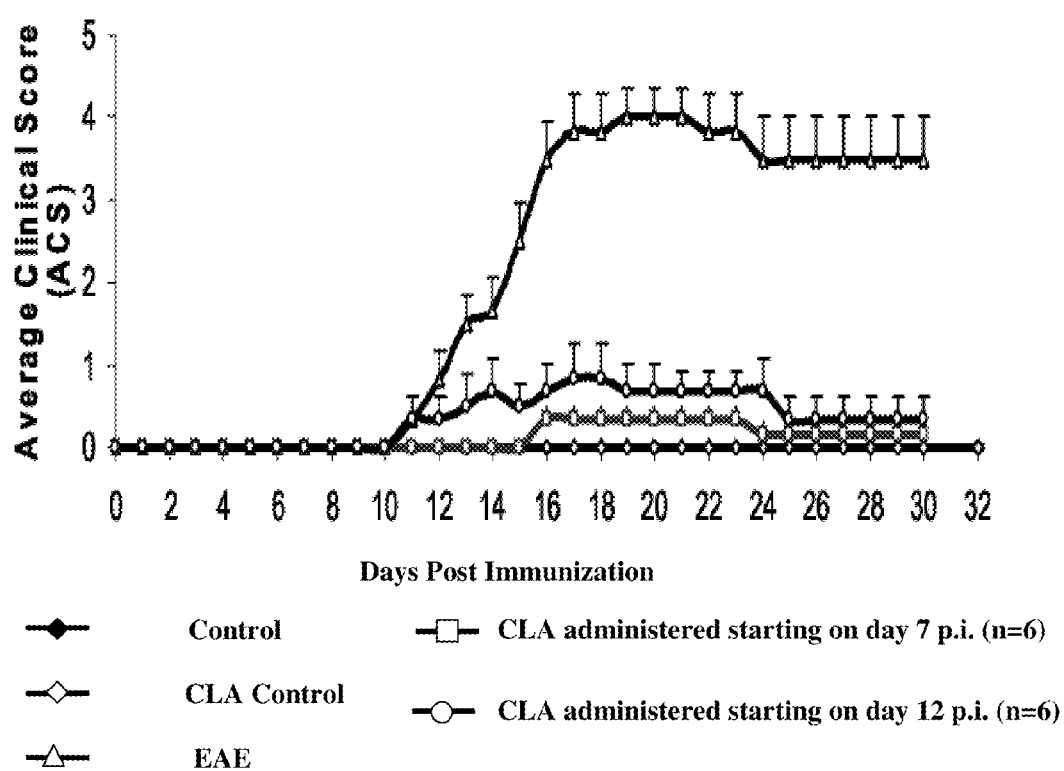
FIG. 7 shows the effects of the progression of EAE in mice as reported in Experiment 4 herein, and the effectiveness of CLA treatment in decreasing and/or slowing the progess of the disease.

Expression of Calpain in Spinal Cord White Matter: Expression of calpain was determined in spinal cord tissues collected from all experimental and control groups of mice at the end of the experiment. Sections of paraformaldehyde-fixed tissues were stained with antibodies against calpain (FITC conjugated), CD11b (MΦ/microglia marker)(Texas Red-conjugated) and CD45 (leukocyte common antigen) (FITC-conjugated). Referring to FIG. 5, six 10 μm sections were stained with anti-calpain antibody and specific cell marker antibodies (CD45, CD11b). Positive staining for calpain (A, B, C); cells positive for MΦ/microglia marker (CD11b$^+$) (D, E, F); cells positive for leukocyte common antigen (CD 45$^+$)(G, H, I). 20× magnification. The results shown in FIG. 5 indicate that enzyme expression was elevated in untreated EAE mice (FIG. 5B) as compared with CLA-treated EAE mice (FIG. 5C). The presence of MΦ/microglia, as shown by CD11b$^+$ cells, was also higher in untreated EAE mice (FIG. 5E) than CLA-treated EAE (FIG. 5F) and CFA control mice (FIG. 5G). All leukocytes including MΦ, but not microglia, are stained with CD45. CD45$^+$ cells were higher in untreated EAE mice (FIG. 5I) than CFA control mice (FIG. 5H), but only marginally higher than CLA-treated EAE mice (FIG. 5J).

Experiment 3: To Investigate If an Increase in Dose and Frequency of CLA-Treatment Can Improve EAE Suppression After the Disease Process has Already Started.

To induce EAE, mice were each inoculated once with MOG aa35-55 in Complete Freund's Adjuvant (CFA) and Pertussis toxin as previously described. Thirty 7 to 8-week-old female C57BL/6J mice (Jackson Laboratories, Bar Harbor, Mass.) were used in this experiment. Of these, eighteen mice were divided into three groups of 6 mice; 1) MOG/CFA/PT, 2) MOG/CFA/PT treated with CLA on day 7 post-immunization (pi), and 3) mice not treated with CLA until each MOG/CFA/PT mouse showed signs of EAE (stage 2). Controls included two groups of 4 mice for CLA only and CFA/PT only and 4 were left as normal controls. CLA was dissolved in PBS and each mouse in the treatment group was injected i.p. with 200 μl of PBS containing 0.5 mg of CLA every 12 hours until the end of the experiment on day 25 pi. Mice were evaluated daily for clinical signs and symptoms of EAE and graded on a 0-6 scale for up to 25 days after inoculation as detailed above. Scores of asymptomatic mice (score=0) were included in the calculation of the daily mean clinical score for each group.

Results:

For the first 9 days no mice showed signs of EAE. Starting on day 10 pi, a few mice from the untreated MOG/CFA group showed signs of the disease. On day 12 and onward, other mice started to show signs of EAE. D7 CLA-treated MOG/CFA mice, however, had a delayed onset of the disease and did not show signs until day 15 pi. These mice also displayed milder symptoms of EAE and did not develop severe paralysis of the limbs (stages 3 and 4). Their neurologic deficit was limited to mild weakness of their hind limbs and a floppy tail. Data were plotted as the daily average clinical scores (ACS) for all mice in a particular treatment or control group. Results are presented in FIG. 6.

Severe acute clinical EAE was induced in MOG/CFA inoculated mice (top line) and a significant reduction in clinical EAE was observed in D7 CLA-treated MOG/CFA mice. The ACS of untreated animals was 2.85 (on day 17 pi) versus an ACS of 0.5 for D7 CLA-treated mice. These results are statistically significant ($\tau$-test p<0.005). The clinical score of treated mice fluctuated, remained low over the remaining days, and was less than one on day 25 pi when the experiment was terminated. Furthermore, MOG/CFA mice who received their twice daily treatments with CLA after they developed signs of stage 2 EAE showed an ACS of 1.60 on day 17 pi. These results were also statistically significant ($\tau$-test p<0.05). The clinical score of these CLA-treated mice also fluctuated over the remaining days, and was less than two on day 25 pi when the experiment was terminated. CLA only, CFA only and normal mice remained healthy.

These results indicate that CLA treatment influenced the clinical outcome of mice in which EAE had been induced. If administered prior to the onset of symptoms (day 7 post-immunization), the symptoms developed later and were less severe than those that were given CLA after symptoms were detected. Mice that were treated with CLA after symptoms developed showed lower average clinical scores than EAE mice that were left untreated.

Experiment 4: Investigation of the Effects of Treatment with CLA on Axonal Degeneration During the Chronic Phase of EAE in Mice.

The chronic phase of EAE occurs after the clinical score of an affected mouse reaches a plateau at the highest level of the acute phase of the disease. In this chronic phase, more extensive damage occurs to nerve axons, beyond the demyelination observed in the acute phase of the disease (22). EAE was induced in 7-8 week-old female C57BL/6J "mice" by subcutaneous (s.c.) injection in each flank with 100 μl of an emulsion containing incomplete Freund's Adjuvant supplemented with 500 μg heat inactivated mycobacterium tuberculosis (Sigma St. Louis, Mo.) and 300 μg MOG 35-55. 100 ng of Pertussis toxin (PT) was given intraperitoneally on days 0 and 2 post-immunization. Thirty mice were divided into five groups:

1.) MOG/CFA/PT (6 mice)
2.) MOG/CFA/PT treated with CLA on day 7 post immunization. (6 mice)
3.) MOG/CFA/PT treated with CLA on day 12 post immunization (6 mice)
4.) control, non-immunized, mice that received 2 mg CLA (4 mice), and
5.) control, non-immunized, mice that received phosphate buffered saline (PBS) instead of CLA (6 mice).

For the mice in the CLA-treated groups, CLA was administered i.p. at an initial dose of 2 mg/mouse, followed by 2 mg/mouse/day until the end of the experiment, which lasted 30 days.

Results:

Clinical evaluation: Clinical severity was scored using the system described in experiment 1, and the results are plotted in FIG. 7. For the untreated EAE group, the clinical scores plateau at approximately day 17, at which point the mice are in the chronic phase of EAE, and the clinical scores of the EAE mice remained close to this level out to day 30 of the experiment, indicating that these mice have entered the chronic phase of EAE. EAE mice treated with 2 mg. CLA at either day 7 (prior to onset of disease) or day 12 (after onset of disease) showed significant improvements in their clinical scores, with clinical scores reaching maxima below 0.5 and 1.0, for the day-7 and day 12 groups, respectively.

Figure 8:
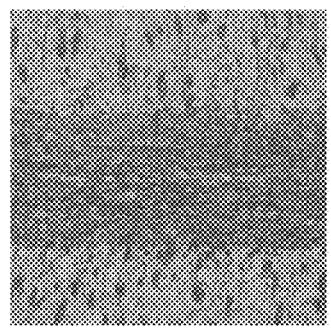
FIG. 8 shows the visible effects of EAE on neuronal axons in mice, and the effectiveness of CLA treatment in decreasing and/or slowing the progess of the disease.
Figure 8:
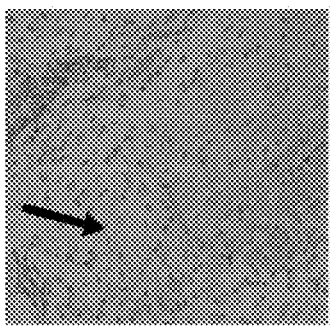
Figure 8:
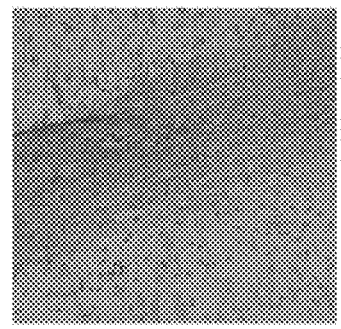
Figure 8:
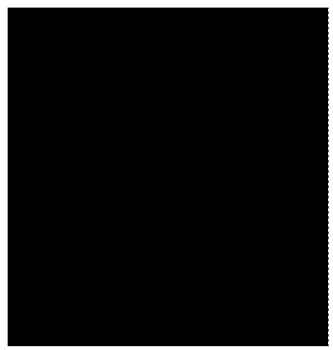
Figure 8:
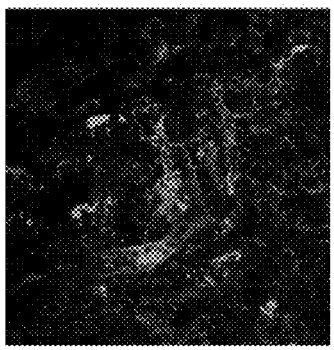
Figure 8:
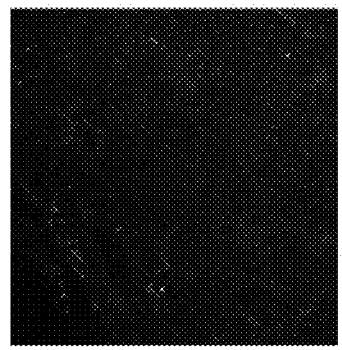

Evaluation of axonal integrity using LFB staining: Spinal cord tissue was taken from mice at day 30 post-immunization, approximately 13 days into the chronic phase of EAE. Myelin is stained a blue color by LFB, and the appearance of a normal myelin-coated axon, taken from spinal cord tissue, is shown longitudinally in FIG. 8A. LFB staining of spinal cord axons from EAE mice (FIG. 8) shows that axonal integrity has been severely compromised. In contrast, the CLA-treated mice show a marked improvement in axonal integrity, resulting in an appearance closer to that of normal axons (FIG. 8C).

Effects on accumulation of amyloid precursor protein: The appearance of significant amounts of amyloid precursor protein (APP) within axons indicates that axonal transport has been disrupted and that axons are severely injured. Spinal cord tissue taken from mice at day 30 was stained with a fluorescently-labeled anti-APP antibody. FIG. 8D shows the absence of fluorescently signal due to the absence of APP in normal, healthy axons. FIG. 8E shows bright green fluorescence due to accumulation of APP in axons of EAE mice, indicative of axonal injury caused by EAE. Treatment of the EAE mice with CLA reduces accumulation of APP in the mouse axons (FIG. 8F).

Experiment 5: Effects of Administering the Acetal Prodrug Form on the Progression of EAE in Mice.

The acetal prodrug form of CLA (CLA-acetal) is not believed to be an inhibitor of calpains. When administered orally to animals, it can be converted to the aldehyde form, CLA, in vivo, thereby enabling the formation of the hemithioacetal bond between CLA and the active-site cysteine of calpain, a bond that is required for inhibition of calpains by CLA and other aldehyde inhibitors. To determine the efficacy of CLA-acetal in treating EAE, CLA-acetal was administered orally to EAE mice and the mice were evaluated clinically, using the same procedures employed in experiments 1-4. To induce EAE, the mice were each inoculated once with MOG aa35-55 in Complete Freund's Adjuvant (CFA) and Pertussis toxin as described in Example I, Experiment 4. 24 mice were divided into four groups of 6 mice each:

1.) MOG/CFA/PT
2.) MOG/CFA/PT treated orally with CLA-acetal on day 7 post immunization.
3.) MOG/CFA/PT treated orally with CLA-acetal on day 12 post immunization, and
4.) control, non-immunized, mice that received phosphate buffered saline (PBS) instead of CLA.

For the mice in the CLA-treated groups, CLA was administered orally at an initial dose of 2.0 mg/mouse, followed by 2.0 mg/mouse/day until the end of the experiment, which lasted 20 days.

Results

Figure 9:
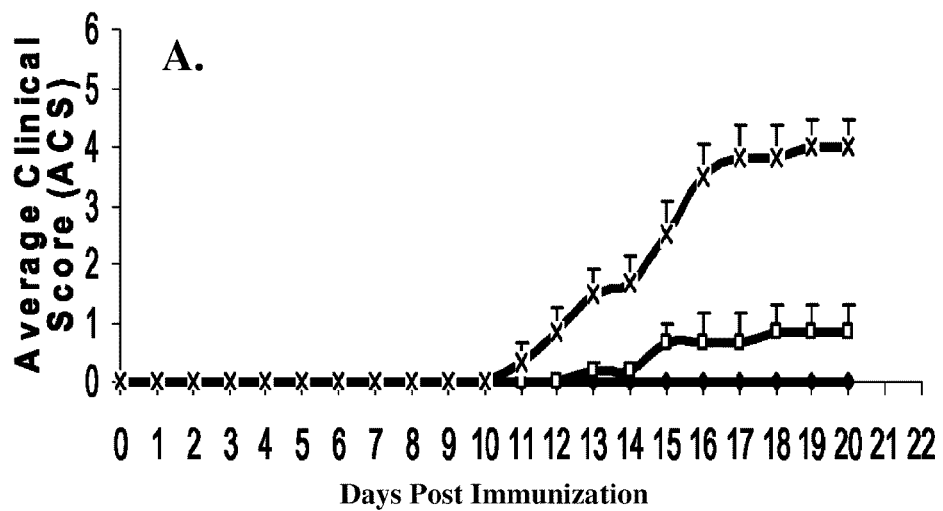
FIG. 9 shows the results reported in Experiment 5 herein, and the effectiveness of the CLA-acetal prodrug in decreasing and/or slowing the progess of EAE in mice.
Figure 9:
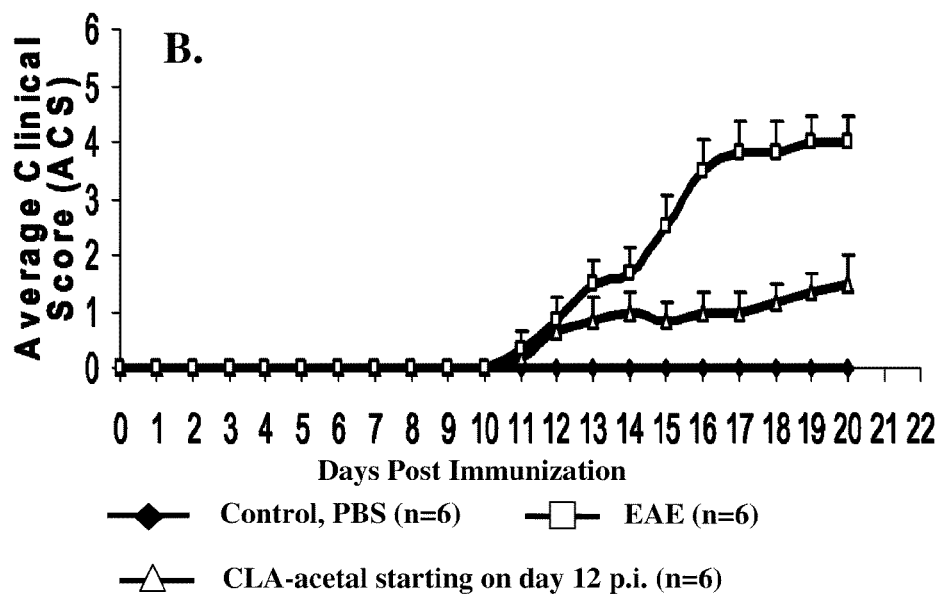

The results of the clinical evaluation are shown in FIG. 9. The clinical scores are markedly reduced when CLA-acetal is administered orally to EAE mice, either before the onset of symptoms (panel A, day 7 p.i.), or after the onset of symptoms (panel B, day 12 p.i.). The magnitude of the effect observed is similar to the effect of administering CLA i.p. (Experiment 4), with a peak clinical score of approximately 1 compared to a peak score of 4 in the EAE group. This result indicates that the CLA-acetal is probably converted to CLA after ingestion by the mice, showing that CLA-acetal is an effective prodrug for treating EAE.

Experiment 6. Use of CLA to Prevent or Treat Acoustic Trauma in Animals Exposed to Very High Levels of Noise.

Figure 10:
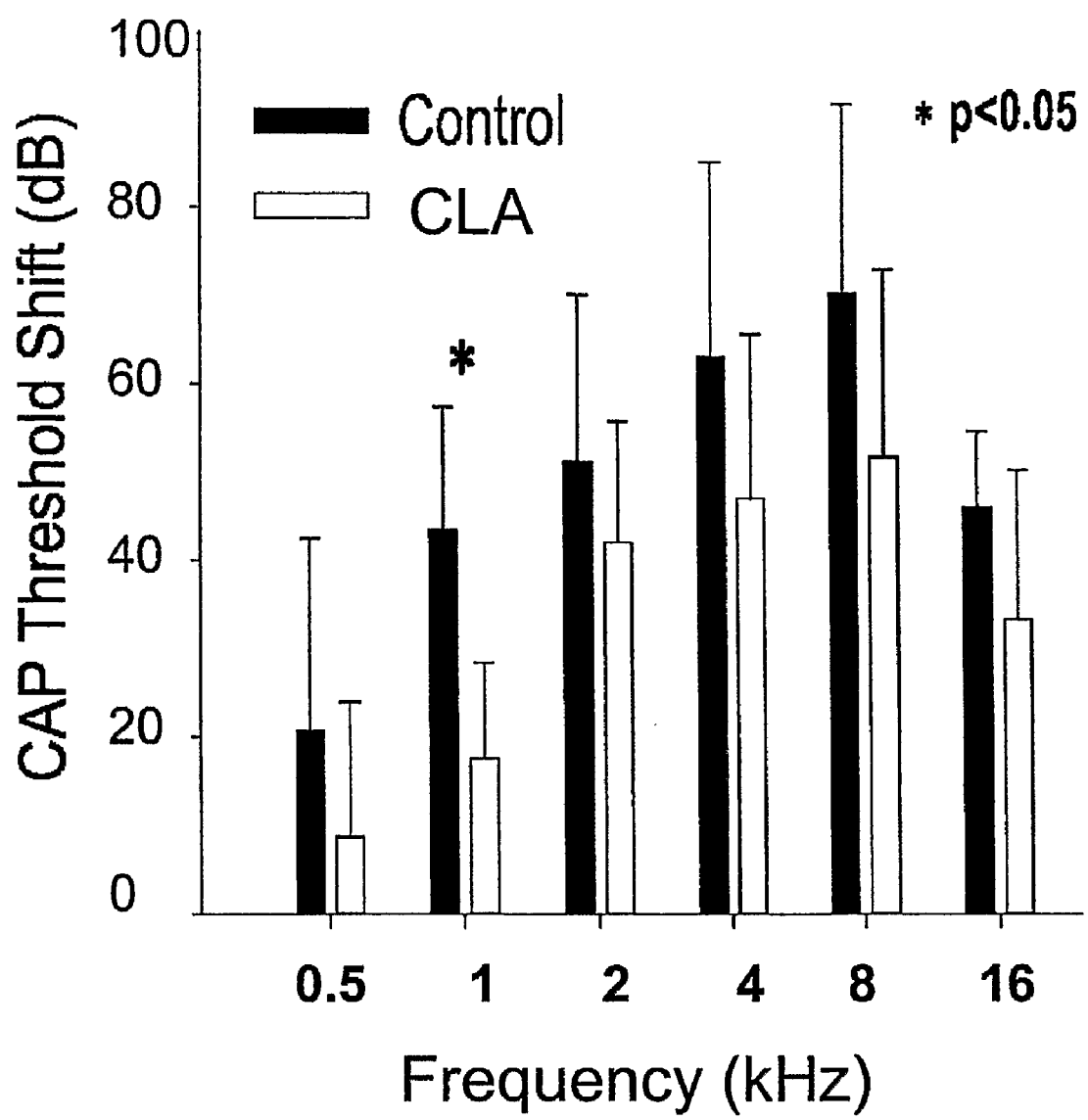
FIG. 10 shows the use of CLA to prevent or treat acoustic trauma in chinchillas as described in Experiment 6, by measurements of compound action potentials (CAP).
Figure 11:
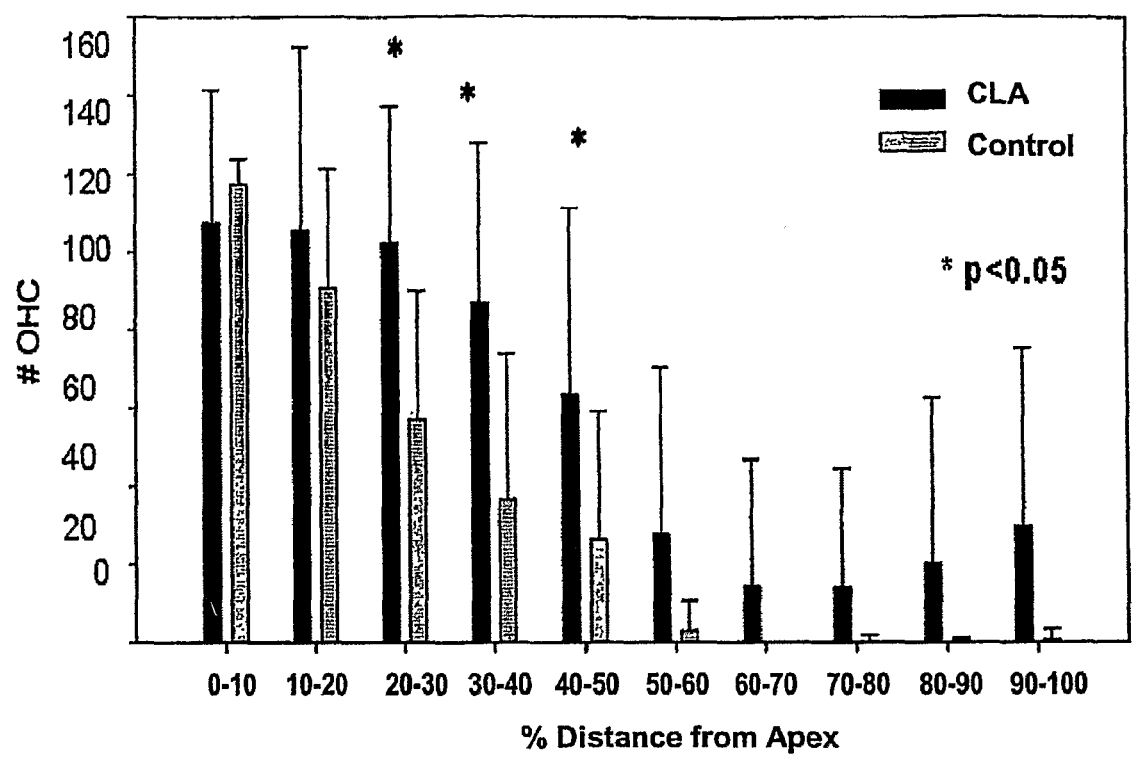
FIG. 11 shows shows the use of CLA to prevent or treat acoustic trauma in chinchillas as described in Experiment 6, by measurement of the numbers of outer hair cells (#OHC) that were counted as a function of the distance from the apex of the cochlea.

Twelve chinchillas were divided into treatment and control groups (six animals each). The treatment groups received 7 mg/kg/day CLA i.p., for seven days. The control groups received an identical volume of PBS vehicle. Starting on day 0, all of the animals were exposed to a 105 decibel sound pressure level (SPL) noise with a frequency band centered on 4 kilohertz (kHz). The noise exposure lasted for 48 hours, ending two days after the beginning of the dose. Approximately 4 weeks after the noise exposure and dosing, the animals were anesthetized, tracheotimized, and placed upon a heating pad (37 degrees C.). A silver-ball electrode was attached to the round window of the left and right ears to record the compound action potential (CAP). CAP input functions were recorded at 0.5, 1, 2, 4, 8, 16 kHz tone burst levels generated by a digital-to-analog converter attached to a computer. The CAP threshold shift is the change in sound level required to generate an action potential at the electrode subsequent to noise exposure, and increases in the threshold shift reflect increased hearing loss. As is shown in FIG. 10, treatment with CLA decreased the CAP threshold shift in the treated vs. control groups, indicating that CLA treatment provided protection against hearing loss. After the CAP threshold shifts were measured, the animals were decapitated, and the cochleae were removed. The hair cells from 11 cochleae were evaluated histologically. The cochleae were opened, stained for 30 minutes with a stain that detects succinate hydrogenase activity, fixed in 10% formalin for 24 hours, and dissected on a flat surface. The numbers of outer hair cells (#OHC) were counted as a function of the distance from the apex of the cochlea. The results are shown in FIG. 11, which indicates that CLA treatment resulted in an increase in the number of outer hair cells at all distances from the apex, with the most significant effects noted at distances ranging from 20-50% of the maximum. This increase in hair cells is an indication that CLA protects outer hair cells that are damaged from acoustic trauma, thereby protecting against hearing loss.

Experiment 7. Accumulation of CLA in the Rat Retina When Rats are Administered a Single Dose of CLA or CLA-Acetal Male Sprague-Dawley rats (n=5 per time point, weight 200-250 g) were administer 10 mg/kg CLA-acetal by oral gavage, formulated as a 0.6% solution in phosphate-buffered saline. At 0.1, 0.25, 0.5, 1, 2, 4, 8, 12 and 24 hours, the rats were anesthetized, blood samples were collected, and the retinas were isolated. The plasma samples (200 µL) were treated with 1 mL methanol and centrifuged to remove protein. The supernatants from centrifugation were evaporated, and the residue was taken up in 0.02% aqueous ammonium heptafluorobutyrate (1 mL). The retina samples were homogenized, treated with methanol, centrifuged, and evaporated, and the residue was taken up in 0.02% aqueous ammonium heptafluorobutyrate (1 mL). The plasma and retinal concentrations of CLA and CLA-acetal were determined by liquid chromatography followed by turbo ion spray mass spectrometry on an MDS-Sciex API 4000 triple-quadropole mass spectrometer equipped with a turbo ion spray source. Elution peaks yielding ions corresponding to CLA or CLA-acetal were integrated and used to determine the amount of compound present, by reference to standards. Data reduction was performed using Sciex Analyst version 1.3 software. The peak concentrations ($C_{max}$) were estimated from the concentrations of CLA measured over time. The concentrations of CLA are much higher in retina than in plasma (Table 1), indicating that the acetal prodrug is converted in vivo to the CLA aldehyde and taken up in retina.

TABLE 1

Peak concentrations of CLA acetal and CLA (aldehyde) observed in rat plasma and retina after oral administration of CLA-acetal.

| Biological Matrix | $C_{max}$, nM CLA-acetal | $C_{max}$, nM CLA |
|---|---|---|
| Plasma | 120 | 12 |
| Retina | 5 | 67 |

Throughout this application, various publications are referenced. The disclosures of these publications in their entireties are hereby incorporated by reference into this application in order to more fully describe, enable, and support the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary and descriptive, but not limiting on the following claims.

REFERENCES

1. Amor S, Groome N, Linington C, Morris M M, Dornmair K, Gardinier M V, Matthieu J M, Baker D. Identification of epitopes of myelin oligodendrocyte glycoprotein for the induction of experimental allergic encephalomyelitis in SJL and Biozzi AB/H mice. J Immunol 1994; 153:4349-56.

2. Badalamente M A, Hurst L C, Stracher A. Localization and inhibition of calcium-activated neutral protease (CANP) in primate skeletal muscle and peripheral nerve. Exp Neurol 1987; 98:357-69.

3. Badalamente M, Hurst L C, Stracher A. Neuromuscular recovery using calcium protease inhibition after median nerve repair in primates. Proc Natl Acad Sci USA 1989;86: 5983-6.

4. Badalamente M A, Hurst L C, Stracher A. Neuromuscular recovery after nerve repair: effects of an orally administered peptide in a primate model. J Reconst Microsurg 1995;11:429-37.

5. Badalamente M, Stracher A. Delay of muscle degeneration and necrosis in mdx mice by calpain inhibition. Muscle and Nerve 2000;23:106-11.

6. Benjamins J A, Nedelkoska L, George E B. Protection of mature oligodendrocytes by inhibitors of caspases and calpains. Neurochem Res 2003;28:143-52.

7. Beraud E, Reshef T, Vandenbark A A, Offner H, Fritz R, Chou C-H, Bernard D, Cohen. IR. Experimental autoimmune encephalomyelitis mediated by T lymphocyte lines: genotype of antigen-presenting cells influences immunodominant epitope of basic protein. J Immunol 1986;136:511-17.

8. Brosnan C F, Cammer W, Norton W T, Bloom, B. Protease inhibitors suppress the development of experimental allergic encephalomyelitis. Nature 1980;285:235-7.

9. de Rosbo N, Mendel I, Ben-Nun A. Chronic relapsing experimental autoimmune encephalomyelitis with a delayed onset and an atypical clinical course, induced in PL/J mice by myelin oligodendrocyte glycoprotein (MOG)-derived peptide: preliminary analysis of MOG T cell epitopes. Eur J Immunol 1995;25:985-93.

10. Ding D, Stracher A, Salvi, R J. Leupeptin protects cochlear and vestibular hair cells from gentamicin ototoxicity. Hear Res 2002;164:115-26.

11. Dyment D A, Ebers G C, Sadovnick A D. Genetics of multiple sclerosis. Review. Lancet Neurol 2004;3:104-10.

12. Endoh M, Kunishita T, Nihei J, Nishizawa M, Tabira M. Susceptibility to proteolipid apoprotein and its encephalitogenic determinants in mice. Int Arch Allerg Appl Immunol 1990;92:433-38.

13. Greer J M, Sobel R A, Sette A, Southwood S, Lees M B, Kuchroo V K. Immunogenic and encephalitogenic epitope clusters of myelin proteolipid protein. J. Immunol 1996;156:371-79.

14. Hafler D A. Multiple sclerosis. Review. J Clin Invest 2004;113:788-94.

15. Homer K C, Aurousseau C. Immunoreactivity for taurine in the cochlea: its abundance in supporting cells. Hear Res 1997;109:135-42.

16. Huxtable R J. Taurine, past, present and future. Exp Med Biol 1996;403:641-50.

17. Jewel S D, Gienapp I E, Cox K L, Whitacre C. Oral tolerance as therapy for experimental autoimmune encephalomyelitis and multiple sclerosis: Demonstration of T cell anergy. Immunol Cell Biol 1998;76:74-82.

18. Johns T G, Kerlero de Rosbo N, Menon K K, Abo S, Gonzales M F, Bernard C C A. Myelin oligodendrocyte glycoprotein induces a demyelinating encephalomyelitis resembling multiple sclerosis. J Immunol 1995;154:5536-41.

19. Kishi M, Ohkuma S, Kimori M, Kuriyama K. Characteristics of taurine transport system and its developmental pattern in mouse cerebral cortical neurons in primary culture. Biochim Biophys Acta 1988;939:615-23.

20. Koyama Y, Baba A, Iwata H. Characteristics of Cl(−)-dependent L-[35S]cysteic acid transport into rat brain synaptic membrane vesicles. Neurochem Res 1990;15:1153-8.

21. Lahdesmaki P, Oja S S. On the mechanism of taurine transport at brain cell membranes. J Neurochem 1973;20:1411-17.

22. Lassmann H. Axonal injury in multiple sclerosis. J Neurol Neurosurg Psychiatry 2003;74:695-7.

23. Lutton International Working Group for Treatment Optimization in MS. Treatment optimization in multiple sclerosis: report of an international consensus meeting. Eur J Neurol 2004;11:43-7.

24. Mendel I, Kerlero de Rosbo N, Ben-Nun A. A myelin oligodendrocyte glycoprotein peptide induces typical chronic experimental autoimmune encephalomyelitis in H-2b mice: fine specificity and T cell receptor Vb expression of encephalitogeniic T cells. Eur J Immunol 1995;25:1951-59.

25. Mokhtarian F. Role of Ia antigen in the induction of adoptively transferred acute and chronic relapsing demyelinating disease in mice. Clin Immunol Immunopath 1988;49:308-17.

26. Mokhtarian F, McFarlin D E, Raine C S. Adoptive transfer of myelin basic protein sensitized T cells produces chronic relapsing demyelinating disease in mice. Nature 1984;309:356-8.

27. Mokhtarian F, Zhang Z, Shi Y, Gonzales E, Sobel R A. Molecular mimicry between a viral peptide and a myelin oligodendrocyte glycoprotein peptide induces autoimmune demyelinating disease in mice. J Neuroimmunol 1999;95:43-54.

28. Nakanishi, H. Involvement of neuronal and microglial proteinases in neuronal death. Neurochem 1999;2: 217-32.

29. Osanai T, Nagai Y. Suppression of experimental allergic encephalomyelitis (EAE) with liposome-encapsulated protease inhibitor: therapy through the blood-brain barrier. Neurochem Res 1984;10:1407-16.

30. Pariat M, Salvat C, Bebien M, Brockly F, Altieri E, Carillo S, Jariel-Encontre I, Piechaczyk M. The sensitivity of c-Jun and c-Fos proteins to calpains depends on conformational determinants of the monomers and not on formation of dimers. Biochem J 2000;345:129-38.

31. Pow D V, Sullivan R, Reye P, Hermanussen S. Localization of taurine transporters, taurine, and (3)H taurine accumulation in the rat retina, pituitary, and brain. Glia 2002;37:153-68.

32. Raine C S, Mokhtarian F, McFarlin D E. Adoptively transferred chronic relapsing experimental autoimmune encephalomyelitis in the mouse. Neuropathologic analysis. Lab Invest 1984;51:534-46.

33. Ray S K, Hogan E L, Banik N L. Calpain in the pathophysiology of spinal cord injury: neuroprotection with calpain inhibitors. Brain Res Rev 2003;42:169-85.

34. Redmond H P, Stapleton P P, Neary P, Bouchier-Hayes D. Immunonutrition: The role of taurine. Nutrition. 1998;14:599-604.

35. Schaecher K, Rocchini A, Dinkins J, Matzelle D D, Banik N L. Calpain expression and infiltration of activated T cells in experimental allergic encephalomyelitis over time: increased calpain activity begins with onset of disease. J Neuroimmunol 2002;129:1-9.

36. Schaecher K E, Shields D C, Banik N L. Mechanism of myelin breakdown in experimental demyelination: a putative role for calpain. Review. Neurochem Res 2001;26:731-7.

37. Shields D C, Banik N L. Upregulation of calpain activity and expression in experimental allergic encephalomyelitis: a putative role for calpain in demyelination. Brain Res 1998;794:68-74.

38. Shields D C, Banik N L. Pathophysiological role of calpain in experimental demyelination. J Neurosci Res 1999; 55:533-41.

39. Shields D C, Schaecher K E, Hogan, E L, Banik N L. Calpain activity and expression increased in activated glial and inflammatory cells in penumbra of spinal cord injury lesion. J Neuroscience Res 2000;61:146-50.

40. Shields D C, Schaecher K E, Saido T C, Banik N L. A putative mechanism of demyelination in multiple sclerosis by a proteolytic enzyme, calpain. Proc Natl Acad Sci USA 1999; 96:11486-91.

41. Shields D C, Tyor W R, Deibler G E, Hogan E L, Banik N L. Increased calpain expression in activated glial and inflammatory cells in experimental allergic encephalomyelitis. Proc Natl Acad Sci USA 1998;95:5768-72.

42. Schuller-Levis G B, Park E. Taurine: new implications for an old amino acid. FEMS Microbiol Lett 2003;226:195-202.

43. Smith M E. Neutral protease activity in lymphocytes of Lewis rats with acute experimental allergic encephalomyelitis. Neurochem Res 1979;4:689-702.

44. Smith M E. Protease inhibitors and the suppression of EAE. Pages 211-26, in Davidson A N, Cyzner M L, (eds), The Suppression of Experimental Allergic Encephalomyelitis and Multiple Sclerosis, Academic Press, New York.

45. Smith M, Amaducci L A. Observations on the effects of protease inhibitors on the suppression of experimental allergic encephalomyelitis. Neurochem Res 1982;7: 541-53.

46. Smith M E, van der Maesen K, Somera F P. Macrophage and microglial responses to cytokines in vitro: phagocytic activity, proteolytic enzyme release, and free radical production. J Neurosci Res 1998;54:68-78.

47. Smith-Norowitz T, Sobel R A, Mokhtarian F. B cells and antibodies in the pathogenesis of myelin injury in Semliki Forest virus encephalomyelitis. Cell Immunol 2000;200:27-35.

48. Sobel R A, Greer J M, Kuchroo V K. Minireview: autoimmune responses to myelin proteolipid protein. Neurochem Res 1994;19:915-21.

49. Stracher A. Molecular principles of drug targeting and delivery, in Molecular Biology and Biotechnology, R A Mayers (ed). VCH Publishers 1995.

50. Stracher A. Calpain Inhibitors as neuroprotective agents in neurodegenerative disorders. Intl Tinnitus J 1998; 3:1-5.

51. Stracher A. Calpain inhibitors as therapeutic agents in nerve and muscle degeneration. Ann NY Acad Sci 1999;884: 52-9.

52. Tuohy V K, Sobel R A, Lees B. Myelin proteolipid protein-induced experimental allergic encephalomyelitis: variations of disease expression in different strains of mice. J Immunol 1988;140:1868-73.

53. Umezawa, H. Enzyme Inhibitors of Microbial Origin, University Park Press, Baltimore. 1972.

54. Weiner H L, Mackin G A, Matsui M, Orav E J, Khoury S J, Dawson D M, Hafler D A. Double-blind pilot trial of oral tolerization with myelin antigens in multiple sclerosis. Science 1993;259: 1321-4.

55. Whitham R H, Jones R E, Hashim G A, Wang C M, Vandenbark A A, Offner H. Location of a new encephalitogenic epitope (residues 43 to 64) in proteolipid protein that induces relapsing experimental autoimmune encephalomyelitis in PL/J and (SJLxPL)F1 mice. J Immunol 1991;147: 3803-08.

56. Zamvil S S, Mitchell D J, Moore C A, Kitamura K, Steinman L, Rothbard J B. T-cell epitope of the autoantigen myelin basic protein that induces encephalomyelitis. Nature 1986;324:258-60.

57. Zhang G X, Yu S, Gran B, Li J, Siglient I, Chen X, Calida D, Ventura E, Kamoun M, Rostami A. Role of IL-12 receptor β1 in regulation of T cell response by APC in experimental autoimmune encephalomyelitis. J Immunol 2003;171:4485-92.

58. Lassmann H. Axonal injury in multiple sclerosis. J Neurol Neurosurg Psychiatry 2003; 74:695-7.

59. Goll D E, Thompson V F, Li H, Wei W, Cong J. "The calpain system," Physiol Rev. July 2003;83(3):731-801.

60. Hernandez A A, Roush W R "Recent advances in the synthesis, design and selection of cysteine protease inhibitors," Curr Opin Chem Biol. August 2002;6(4):459-465.

61. Perrin B J, Huttenlocher A. "Calpain," Int J Biochem Cell Biol. 2002 Jul; 34(7):722-5.

62. Laval S H, Bushby K M "Limb-girdle muscular dystrophies—from genetics to molecular pathology," Neuropathol Appl Neurobiol. April 2004;30(2):91-105.

63. Wagner K R "Genetic diseases of muscle" Neurol Clin. August 2002;20(3):645-78.

64. Vanderklish P W, Bahr B A "The pathogenic activation of calpain: a marker and mediator of cellular toxicity and disease states" Int J Exp Pathol. October 2000;81(5):323-39.

65. Hasselgren P O, Fischer J E "Muscle cachexia: current concepts of intracellular mechanisms and molecular regulation," Ann Surg. January 2001;233(1):9-17.

66. Wang K K, Yuen P W "Calpain inhibition: an overview of its therapeutic potential," Trends Pharmacol Sci. November 1994;15(11):412-9.

67. Ray S K and Banik N L "Calpain and its involvement in the Pathophysiology of CNS injuries and diseases. Therapeutic potential of calpain inhibitors for prevention of neurodegeneration," Current Drug Targets-CNS and Neurological Disorders, 2, 173-189, 2003.

68. Intentionally Blank

69. U.S. Pat. No. 4,742,081

70. U.S. Pat. No. 4,866,040

71. U.S. Pat. No. 5,008,288

72. U.S. Pat. No. 5,876,747

73. Chen T M, Jones H K, "Epimerization study of the L,L- and L,D-diastereoisomers of the calpain inhibitor MDL 28170 by capillary electrophoresis," J Chromatogr B Analyt Technol Biomed Life Sci. Sep. 25, 2004;809(1):31-5.

74. Sengoku T, Bondada V, Hassane D, Dubal S, Geddes J W, Tat-calpastatin fusion proteins transduce primary rat cortical neurons but do not inhibit cellular calpain activity," Exp Neurol. July 2004;188(1):161-70.

75. Kulkarni S, Jackson S P, "Platelet factor XIII and calpain negatively regulate integrin alphaIIbbeta3 adhesive function and thrombus growth," J Biol Chem. July 16, 2004; 279(29):30697-706. Epub May 6, 2004.

76. Liebetrau M, Burggraf D, Martens H K, Pichler M, Hamann G F, "Delayed moderate hypothermia reduces calpain activity and breakdown of its substrate in experimental focal cerebral ischemia in rats," Neurosci Lett. Feb. 26, 2004;357(1):17-20.

77. Pike B R, Flint J, Dave J R, Lu X C, Wang K K, Tortella F C, Hayes R L, "Accumulation of calpain and caspase-3 proteolytic fragments of brain-derived alphaII-spectrin in cerebral spinal fluid after middle cerebral artery occlusion in rats. J Cereb Blood Flow Metab. January 2004;24(1):98-106.

78. Rau S W, Dubal D B, Bottner M, Gerhold L M, Wise P M, "Estradiol attenuates programmed cell death after stroke-like injury," J Neurosci. December 10, 2003;23(36):11420-6.

79. Rami A, Volkmann T, Agarwal R, Schoninger S, Nurnberger F, Saido T C, Winckler J, "beta2-Adrenergic receptor responsiveness of the calpain-calpastatin system and attenuation of neuronal death in rat hippocampus after transient global ischemia," Neurosci Res. December 2003;47(4):373-82.

80. DePetrillo P B, "Calpains inhibitors—a review of the recent patent literature," IDrugs. June 2002;5(6):568-76.

81. Sedarous M, Keramaris E, O'Hare M, Melloni E, Slack R S, Elce J S, Greer P A, Park D S, "Calpains mediate p53 activation and neuronal death evoked by DNA damage," J Biol Chem. Jul. 11, 2003;278(28):26031-8. Epub Apr. 29, 2003.

82. Benjamins J A, Nedelkoska L, George E B, "Protection of mature oligodendrocytes by inhibitors of caspases and calpains," Neurochem Res. January 2003;28(1):143-52.

83. Namura S, Hirt L, Wheeler V C, McGinnis K M, Hilditch-Maguire P, Moskowitz M A, MacDonald M E, Persichetti F, "The HD mutation does not alter neuronal death in the striatum of Hdh(Q92) knock-in mice after mild focal ischemia," Neurobiol Dis. October 2002;11(1):147-54.

84. Arvin K L, Han B H, Du Y, Lin S Z, Paul S M, Holtzman D M, "Minocycline markedly protects the neonatal brain against hypoxic-ischemic injury," Ann Neurol. July 2002;52(1):54-61.

85. Newcomb-Fernandez J K, Zhao X, Pike B R, Wang K K, Kampfl A, Beer R, DeFord S M, Hayes R L, "Concurrent assessment of calpain and caspase-3 activation after oxygen-glucose deprivation in primary septo-hippocampal cultures," J Cereb Blood Flow Metab. November 2001;21(11):1281-94.

86. Srivastava K, Dash D, "Altered membrane fluidity and signal transduction in the platelets from patients of thrombotic stroke," Mol Cell Biochem. August 2001;224(1-2):143-9.

87. Huang Y, Wang K K, "The calpain family and human disease," Trends Mol Med. August 2001;7(8):355-62.

What is claimed is:

1. A method for treating multiple sclerosis in a subject diagnosed with multiple sclerosis comprising administering to the subject an effective amount of cysteyl-leucyl-argininal or a prodrug or a pharmaceutically acceptable salt thereof, wherein the prodrug is formed via the cysteyl-leucyl-argininal reacting with one or more alcohols, and wherein the one or more alcohols comprise at least one of methyl, ethyl, propyl, isopropyl, butyl, isobutyl, penryl, isopentyl, and hexyl.

2. The method of claim 1, wherein at least one of the one or more alcohols is methyl alcohol.

3. The method of claim 1, wherein at least one of the one or more alcohols is ethyl alcohol.

4. The method of claim 1, wherein at least one of the one or more alcohols is propyl alcohol.

5. The method of claim 1, wherein at least one of the one or more alcohols is isopropyl alcohol.

6. The method of claim 1, wherein at least one of the one or more alcohols is butyl alcohol.

7. The method of claim 1, wherein at least one of the one or more alcohols is isobutyl alcohol.

8. The method of claim 1, wherein at least one of the one or more alcohols is pentyl alcohol.

9. The method of claim 1, wherein at least one of the one or more alcohols is isopentyl alcohol.

10. The method of claim 1, wherein at least one of the one or more alcohols is hexyl alcohol.

* * * * *

UNITED STATES PATENT AND TRADEMARK OFFICE
CERTIFICATE OF CORRECTION

| | | |
|---|---|---|
| PATENT NO. | : 7,968,516 B2 | Page 1 of 1 |
| APPLICATION NO. | : 11/663666 | |
| DATED | : June 28, 2011 | |
| INVENTOR(S) | : Alfred Stracher et al. | |

It is certified that error appears in the above-identified patent and that said Letters Patent is hereby corrected as shown below:

In the front page, the term "calpin" in the title should read "calpain".

In the front page, References Cited section, the Sriram *et al.* reference, the term "allerfic" in the reference title should read "allergic".

In Column 29, line 40, the term "Results" should read "Results:".

In Column 33, line 1, the term "Results" should read "Results:".

Signed and Sealed this
Fourth Day of October, 2011

David J. Kappos
*Director of the United States Patent and Trademark Office*